US008507201B2

(12) United States Patent
Cockerill, III et al.

(10) Patent No.: US 8,507,201 B2
(45) Date of Patent: Aug. 13, 2013

(54) **DETECTION OF *BORDETELLA***

(75) Inventors: Franklin R Cockerill, III, Rochester, MN (US); Robin Patel, Rochester, MN (US); Lynne M Sloan, Rochester, MN (US); Sabine Lohmann, Penzberg (DE); Ulrike Salat, Eberfing (DE)

(73) Assignees: Mayo Foundation for Medical Education and Research, Rochester, MN (US); Roche Molecular Systems, Inc., Pleasanton, CA (US)

( * ) Notice: Subject to any disclaimer, the term of this patent is extended or adjusted under 35 U.S.C. 154(b) by 447 days.

(21) Appl. No.: 12/620,095

(22) Filed: Nov. 17, 2009

(65) Prior Publication Data

US 2010/0221715 A1 Sep. 2, 2010

Related U.S. Application Data

(62) Division of application No. 10/754,223, filed on Jan. 9, 2004, now Pat. No. 7,691,571.

(51) Int. Cl.

| | |
|---|---|
| *C12Q 1/68* | (2006.01) |
| *C12P 19/34* | (2006.01) |
| *C07H 21/02* | (2006.01) |
| *C07H 21/04* | (2006.01) |

(52) U.S. Cl.
USPC .......... 435/6.1; 435/91.2; 536/23.1; 536/24.3

(58) Field of Classification Search
None
See application file for complete search history.

(56) References Cited

U.S. PATENT DOCUMENTS

| | | | |
|---|---|---|---|
| 5,702,895 | A | 12/1997 | Matsunaga et al. |
| 5,837,452 | A | 11/1998 | Clark et al. |
| 5,925,517 | A | 7/1999 | Tyagi et al. |
| 6,174,670 | B1 | 1/2001 | Wittwer et al. |
| 6,312,929 | B1 | 11/2001 | McMillan |
| 6,593,093 | B1 | 7/2003 | Uhl et al. |

FOREIGN PATENT DOCUMENTS

| | | |
|---|---|---|
| EP | 0 269 764 | 6/1988 |
| EP | 0 338 591 | 10/1989 |
| EP | 0 526 876 | 2/1993 |
| EP | 1 045 033 | 10/2000 |
| EP | 1 160 333 | 12/2001 |
| WO | WO 98/48046 | 10/1998 |
| WO | WO 99/19466 | 4/1999 |
| WO | WO 99/45155 | 9/1999 |
| WO | WO 00/37646 | 6/2000 |
| WO | WO 00/70096 | 11/2000 |
| WO | WO 01/12803 | 2/2001 |
| WO | WO 01/23604 | 4/2001 |
| WO | WO 02/18660 | 3/2002 |
| WO | WO 02/34771 | 5/2002 |
| WO | WO 02/061141 | * 8/2002 |
| WO | WO 02/061390 | 8/2002 |
| WO | WO 02/092818 | 11/2002 |
| WO | WO 03/025216 | 3/2003 |
| WO | WO 03/068918 | 8/2003 |
| WO | WO 03/93306 | 11/2003 |

OTHER PUBLICATIONS

"LightCycler-FastStart DNA Master Hybridization Probes," 1999 Roche Diagnostics GmbH Technical Manual, retrieved from the internet on Feb. 6, 2004: http://www.roche-applied-science.com.
Al-Robaiy et al., "Rapid Competitive PCR Using Melting Curve Analysis for DNA Quantification," *BioTechniques*, 2001, 31:1382-1388.
Arthur et al., "*Enterococcus faecium* transposon Tn1546 transposase, resolvase, vanR, vanS, vanH, vanA, vanX, vanY and teicoplanin resistance protein (vanZ) genes, complete cds," 1993, database accession No. M97297.
Bélanger et al., "Rapid Detection of Shiga Toxin-Producing Bacteria in Feces by Multiplex PCR with Molecular Beacons on the Smart Cycler," *J. Clin. Microbiol.*, 2002, 40:1436-1440.
Bellin et al., "Rapid Detection of Enterohemorrhagic *Escherichia coli* by Real-Time PCR with Fluorescent Hybridization Probes," *J. Clin. Microbiol.*, 2001, 39:370-374.
Bergeron et al., "Rapid Detection of Group B Streptococci in Pregnant Women at Delivery," *N. Eng. J. Med.*, 2000, 343(3):175-179.
Brink et al., "Nucleic Acid Sequence-Based Amplification, A New Method for Analysis of Spliced and Unspliced Epstein-Barr Virus Latent Transcripts, and Its Comparison with Reverse Transcriptase PCR," *J. Clin. Microbiol.*, 1998, 36(11):3164-3169.
Buck et al., "Design strategies and performance of custom DNA sequencing primers," *Biotechniques*, 1999, 27:528-536.
Caplin et al., "LightCycler™ hybridization probes; The most direct way to monitor PCR amplification for quantification and mutation detection," *Biochemica*, 1999, 1:5-8.
Chen et al., An Automated Fluorescent PCR Method for Detection of Shiga Toxin-Producing *Escherichia coli* in Foods,: *Appl. Environ. Microbiol.*, 1998, 64:4210-4216.
Didenko, "DNA Probes Using Fluorescence Resonance Energy Transfer (FRET): Designs and Applications," *BioTechniques*, 2001, 31:1106-1121.
Espy et al., "Detection of Smallpox Virus DNA by LightCycler PCR," *J. Clin. Microbiol.*, 2002, 40(6):1985-1988.
Espy et al., "Diagnosis of Herpes Simplex Virus Infections in the Clinical Laboratory by LightCycler PCR," *J. Clin. Microbiol.*, 2000, 38(2):795-799.
Espy et al., "Diagnosis of Varicella-Zoster Virus Infections in the Clinical Laboratory by LightCycler PCR," *J. Clin. Microbiol.*, 2000, 38(9):3187-3189.
Espy et al., "Quantification of Epstein-Barr Virus (EBV) Viral Load in Transplant Patients by LightCycler PCR," *Abstracts of the General Meeting of the American Society for Microbiology*, 101st General Meeting, May 20-24, 2001, 101:182, Abstract No. C-148.
Farrell et al., "Nested duplex PCR to detect *Bordetella pertussis* and *Bordetella parapertussis* and its application in diagnosis of Pertussis in nonmetropolitan southeast Queensland, Australia," *J. Clin. Micro.*, Mar. 1999, 37(3):606-610.
Grisold et al., "Detection of Methicillin-Resistant *Staphylococcus aureus* and Simultaneous Confirmation by Automated Nucleic Acid Extraction and Real-Time PCR," *J. Clin. Microbiol.*, 2002, 40:2392-2397.
Holland et al., "PCR Detection of *Escherichia coli* 0157:H7 Directly from Stools: Evaluation of Commercial Extraction Methods for Purifying Fecal DNA," *J. Clin. Microbiol.*, 2000, 38:4108-4113.

(Continued)

*Primary Examiner* — Teresa E Strzelecka
(74) *Attorney, Agent, or Firm* — Fish & Richardson P.C.

(57) ABSTRACT

The invention provides methods to detect *Bordetella pertussis* and/or *Bordetella parapertussis* in a biological sample. Primers and probes for the differential detection of *B. pertussis* and *B. parapertussis* are provided by the invention. Articles of manufacture containing such primers and probes for detecting *B. pertussis* and/or *B. parapertussis* are further provided by the invention.

6 Claims, No Drawings

(56) References Cited

OTHER PUBLICATIONS

Huletsky et al., "Rapid Detection of Vancomycin-Resistant Enterococci Directly from Rectal Swabs by Real-Time PCR Using the Smart Cycler," *Abstracts of the Interscience Conference on Antimicrobial Agents and Chemotherapy*, Chicago, Illinois, Sep. 22-25, 2001, 41:409. (Abstract K-1195).

Ito et al., "Staphylococcus aureus DNA, type-I staphylococcal cassette chromosome mec," 1999, database accession No. AB033763.

Ke et al., "Development of conventional and real-time PCR assays for the rapid detection of group B streptococci," *Clin. Chem.*, 2000, 46(3):324-331.

Livak et al., "Oligonucleotides with Fluorescent Dyes at Opposite Ends Provide A Quenched Probe System Useful for Detecting PCR Product and Nucleic Acid Hybridization," *Genome Research*, 1995, 4:357-362.

Longo et al., "Use of uracil DNA glycosylase to control carry-over contamination in polymerase chain reactions," *Gene*, 1990, 93:125-128.

Machiels et al., "New Protocol for DNA Extraction of Stool," *BioTechniques*, 2000, 28:286-290.

McLafferty et al., "Nucleotide sequence and characterization of a repetitive DNA element from the genome of *Bordetella pertussis* with characteristics of an insertion sequence," *J. Gen. Microbiol.*, 1988, 134:2297-2306.

McOrist et al., "A comparison of five methods for extraction of bacterial DNA from human faecal samples," *J. Microbiol. Meth.*, 2002, 50:131-139.

Palladino et al., "Rapid Detection of *vanA* and *vanB* Genes Directly from Clinical Specimens and Enrichment Broths by Real-Time Multiplex PCR Assay," *J. Clin. Microbiol.*, 2003, 41:2483-2486.

Palladino et al., "Real-time PCR for the rapid detection of *vanA* and *vanB* genes," *Diagnostic Microbiology and Infectious Disease*, 2003, 45:81-84.

Patel et al., "*Enterococcus faecalis* vancomycin resistance protein vanB gene, partial cds," 1997, database accession No. U72704.

Patel et al., "*Enterococcus faecium* vancomycin resistance protein B (vanB) gene, partial cds," 1997, database accession No. U94528.

Petrich et al., "Direct detection of *vanA* and *vanB* genes in clinical specimens for rapid identification of vancomycin resistant enterococci (VRE) using multiplex PCR," *Molecular and Cellular Probes* 1999, 13:275-281

Ramotar et al., "Direct Detection of Verotoxin-Producing *Escherichia coli* in Stool Samples by PCR," *J. Clin. Microbiol.*, 1995, 33:519-524.

Reischl et al., "Rapid Identification of Methicillin-Resistant *Staphylococcus aureus* and Simultaneous Species Confirmation Using Real-Time Fluorescence PCR," *J. Clin. Microbiol.*, 2000, 38:2429-2433.

Ryncarz et al., "Development of a High-Throughput Quantitative Assay for Detecting Herpes Simplex Virus DNA in Clinical Samples," *J. Clin. Microbiol.*, 1999, 37:1941-1947.

Sample et al., "Two Related Epstein-Barr Virus Membrane Proteins are Encoded by Separate Genes," *J. Virol.*, 1989, 63(2):933-937.

Sloan et al., "Evaluation of a Combined LightCycler Assay for the Detection of vanA, vanB, and vanB-2/3 Genes in Enterococci," *Abstracts of the General Meeting of the American Society for Microbiology*, 2002, 102:143 (Abstract C-242).

Smith, "Application of Lightcycler Real Time PCR in Clinical Virology," *Clin. Chem. Lab. Med.*, 2001, Special Supplement, 39:S60, Abstract No. ISW14-2.

Telenti et al., "Detection of Epstein-Barr Virus by Polymerase Chain Reaction," *J. Clin. Microbiol.*, 1990, 28(10):2187-2190.

Van Der Hoek et al., "Isolation of Human Immunodeficiency Virus Type 1 (HIV-1) RNA from Feces by a Simple Method and Difference between HIV-1 Subpopulations in Feces and Serum," *J. Clin. Microbiol.*, 1995, 33:581-588.

Van der Zee et al., "Characterization of IS1001, an insertion sequence element of *Bordetella parapertussis*," *J. Bacteriol.*, 1993, 175:141-147.

Van der Zee et al., "Polymerase chain reaction assay for pertussis: simultaneous detection and discrimination of *Bordetella pertussis* and *Bordetella parapertussis*," *J. Clin. Microbiol.*, 1993, 31:2134-2140.

Authorized Officer Kenneth R. Horlick, International Search Report re PCT/US02/02896, mailed 11 Jun. 3, 2002, 2 pages.

Authorized Officer Kenneth R. Horlick, Written Opinion of the International Search Authority re PCT/US02/02896, mailed Nov. 25, 2002, 5 pages.

Authorized Officer Kenneth R. Horlick, International Preliminary Examination Report re PCT/US02/02896, mailed Mar. 5, 2003, 4 pages.

* cited by examiner

DETECTION OF BORDETELLA

CROSS REFERENCE TO RELATED APPLICATIONS

This application is a Divisional application and claims priority under 35 U.S.C. §120 of U.S. application Ser. No. 10/754,223 filed Jan. 9, 2004 now U.S. Pat. No. 7,691,571.

TECHNICAL FIELD

This invention relates to bacterial diagnostics, and more particularly to detection of Bordetella.

BACKGROUND

Whooping cough, caused by Bordetella pertussis, is presently one of the ten most common causes of death from infectious disease worldwide. Patients first present with a common cold and a cough. However, the disease progresses to paroxysmal coughing followed by a characteristic inspiratory whoop. Secondary symptoms arising from bacterial pneumonia, neurological complications (i.e., seizures and encephalopathy), and pressure effect complications (i.e., pneumothorax, epistaxis, subdural hematomas, hernias, and rectal prolapse) can also occur. From the onset of initial symptoms, the disease can take 6-8 weeks to resolve. Bordetella parapertussis is closely related to B. pertussis and may cause a similar illness, especially in children; however, the symptoms are less severe and are generally of shorter duration than B. pertussis.

Pertussis and its associated complications were a major cause of infant and childhood mortality until the introduction of the diphtheria-tetanus-pertussis (DTP) vaccine in the 1940s. Widespread use of the vaccine in the American population resulted in a 98% decrease in the incidence of pertussis. According to the Centers for Disease Control (CDC; Atlanta, Ga.), there has been a resurgence of pertussis, and the incidence of pertussis in the general population has been on the rise since 1991. There was an 82% increase in total cases reported to the CDC in 1993 compared to the same period in 1992 (1992=3004; 1993=5457). In 1992, there were outbreaks of pertussis in Massachusetts and Maryland, and in 1994 there was an outbreak of erythromycin-resistant B. pertussis described in Arizona. This trend is also being seen outside the United States. In 1996, the Netherlands had an outbreak of pertussis, reporting 12 times the number of cases seen in 1995 (1995=341; 1996=4231).

Many cases of B. pertussis go undiagnosed and unreported. While pertussis is highly communicable and can cause severe disease, symptoms in older children and adults, including those previously immunized, may be difficult to differentiate from the nonspecific symptoms of bronchitis and upper respiratory tract infections. Clinical diagnosis of pertussis is complicated by the fact that the characteristic cough (whoop) is rarely observed in infants and adult patients.

SUMMARY

Methods of the invention can be used to rapidly identify B. pertussis and/or B. parapertussis from a biological sample for differential diagnosis of pertussis infection. Nasopharyngeal swabs and aspirates can be treated to release the DNA from Bordetella species in the sample. Using specific primers and probes, the method includes amplifying and monitoring the development of specific template nucleic acid using fluorescence resonance emission technology (FRET).

In one aspect, the invention provides a method for detecting the presence or absence of Bordetella pertussis and/or B. parapertussis in a biological sample from an individual. The method includes performing at least one cycling step of amplifying and hybridizing. The amplifying step includes contacting the sample with a pair of IS481 primers and/or a pair of IS1001 primers to produce an IS481 and/or an IS1001 amplification product, respectively, if IS481 and/or IS1001 nucleic acid molecules are present in the sample. The hybridizing step includes contacting the sample with a pair of IS481 probes and/or a pair of IS1001 probes. Generally, the members within each pair of IS481 and IS1001 probes hybridize within no more than five nucleotides of each other. Typically, a first IS481 probe of the pair of IS481 probes is labeled with a donor fluorescent moiety and a second IS481 probe of the pair of IS481 probes is labeled with a corresponding acceptor fluorescent moiety. Likewise, a first IS1001 probe of the pair of IS1001 probes is labeled with a donor fluorescent moiety and a second IS1001 probe of the pair of IS1001 probes is labeled with a corresponding acceptor fluorescent moiety. The donor fluorescent moiety and/or the acceptor fluorescent moieties on the IS481 and the IS1001 probes can be different.

The method further includes detecting the presence or absence of FRET between the donor fluorescent moiety of the first IS481 probe and the corresponding acceptor fluorescent moiety of the second IS481 probe and/or between the donor fluorescent moiety of the first IS1001 probe and the corresponding acceptor fluorescent moiety of the second IS1001 probe. The presence of FRET usually indicates the presence of B. pertussis and/or B. parapertussis in the biological sample, while the absence of FRET usually indicates the absence of B. pertussis or B. parapertussis in the biological sample.

The method can additionally include determining the melting temperature between the IS481 probes and the IS481 amplification product and/or between the IS1001 probes and the IS1001 amplification product. The melting temperature(s) further confirms the presence or absence of B. pertussis and the presence or absence of B. parapertussis in the sample.

In another aspect of the invention, the above-described method can be performed to detect B. pertussis using primers and probes that hybridize to IS481 nucleic acid molecules. Alternatively, the above-described method can be performed to detect B. parapertussis using primers and probes that hybridize to IS1001 nucleic acid molecules.

In one aspect of the invention, there is provided a pair of IS481 primers including a first IS481 primer and a second IS481 primer. A first IS481 primer can include the sequence 5'-CCA GTT CCT CAA GGA CGC-3' (SEQ ID NO:1), and the second IS481 primer can include the sequence 5'-GAG TTC TGG TAG GTG TGA GCG TA-3' (SEQ ID NO:2). A first IS481 probe can include the sequence 5'-CAC CGC TTT ACC CGA CCT TAC CGC CCA C-3' (SEQ ID NO:3), and a second IS481 probe can include the sequence 5'-GAC CAA TGG CAA GGC CGA ACG CTT CAT C-3' (SEQ ID NO:4). In another embodiment, a second IS481 probe can include the sequence 5'-GAC CAA TGG CAA GGC TCG AAC GCT TCA TC-3' (SEQ ID NO:11).

In another aspect of the invention, there is provided a pair of IS1001 primers including a first IS1001 primer and a second IS1001 primer. A first IS1001 primer can include the sequence 5'-GGC GAT ATC AAC GGG TGA-3' (SEQ ID NO:5), and the second IS1001 primer can include the sequence 5'-CAG GGC AAA CTC GTC CAT C-3' (SEQ ID NO:6). The invention further provides a first IS1001 probe that can include the sequence 5'-GTT CTT CGA ACT GGG TTG GCA TAC-3' (SEQ ID NO:7), and a second IS1001 probe that can include the sequence 5'-GTC AAG ACG CTG GAC AAG GCT C-3' (SEQ ID NO:8). In another embodiment, a first IS1001 probe can include the sequence 5'-GGT TGG CAT ACC GTC AAG A-3' (SEQ ID NO:12), and a second IS1001 probe can include the sequence 5'-GCT GGA CAA GGC TCG-3' (SEQ ID NO:13).

Representative biological samples include nasopharyngeal swabs, nasopharyngeal aspirates, and throat swabs. Generally, the members of the pair of IS481 probes hybridize within no more than two nucleotides of each other, or within no more than one nucleotide of each other. A representative donor fluorescent moiety is fluorescein, and corresponding acceptor fluorescent moieties include LCT™-Red 640, LCT™-Red 705, Cy5, and Cy5.5. Additional corresponding donor and acceptor fluorescent moieties are known in the art.

In one aspect, the detecting step includes exciting the biological sample at a wavelength absorbed by the donor fluorescent moiety and visualizing and/or measuring the wavelength emitted by the acceptor fluorescent moiety. In another aspect, the detecting step includes quantitating FRET. In yet another aspect, the detecting step is performed after each cycling step (e.g., in real-time).

The above-described methods can further include preventing amplification of a contaminant nucleic acid. Preventing amplification can include performing amplifying steps in the presence of uracil and treating the biological samples with uracil-DNA glycosylase prior to amplifying. In addition, the cycling step can be performed on a control sample. A control sample can include the same portion of the IS481 or IS1001 nucleic acid molecule. Alternatively, a control sample can include a nucleic acid molecule other than an IS481 or IS1001 nucleic acid. Cycling steps can be performed on such a control sample using a pair of control primers and a pair of control probes that are other than IS481 or IS1001 primers and probes. One or more amplifying steps produces a control amplification product. Each of the control probes hybridize to the control amplification product.

In yet another aspect, the invention provides articles of manufacture, or kits. Kits of the invention can include a pair of IS481 primers, a pair of IS481 probes, and a donor and corresponding acceptor fluorescent moiety. For example, a first IS481 primer provided in a kit of the invention can include the sequence 5'-CCA GTT CCT CAA GGA CGC-3' (SEQ ID NO:1), and a second IS481 primer can include the sequence 5'-GAG TTC TGG TAG GTG TGA GCG TA-3' (SEQ ID NO:2). A first IS481 probe provided in a kit of the invention can include the sequence 5'-CAC CGC TTT ACC CGA CCT TAC CGC CCA C-3' (SEQ ID NO:3), and a second IS481 probe can include the sequence 5'-GAC CAA TGG CAA GGC CGA ACG CTT CAT C-3' (SEQ ID NO:4). In another embodiment, a second IS481 probe provided in a kit of the invention can include the sequence 5'-GAC CAA TGG CAA GGC TCG AAC GCT TCA TC-3' (SEQ ID NO:11).

In another aspect of the invention, there is provided an article of manufacture, or kit. Kits of the invention can include a pair of IS1001 primers, a pair of IS1001 probes, and a donor and corresponding acceptor fluorescent moiety. For example, a first IS1001 primer provided in a kit of the invention can include the sequence 5'-GGC GAT ATC AAC GGG TGA-3' (SEQ ID NO:5), and a second IS1001 primer can include the sequence 5'-CAG GGC AAA CTC GTC CAT C-3' (SEQ ID NO:6). A first IS1001 probe provided in a kit of the invention can include the sequence 5'-GTT CTT CGA ACT GGG TTG GCA TAC-3' (SEQ ID NO:7), and the second IS1001 probe can include the sequence 5'-GTC AAG ACG CTG GAC AAG GCT C-3' (SEQ ID NO:8). In another embodiment, a first IS1001 probe provided in a kit of the invention can include the sequence 5'-GGT TGG CAT ACC GTC AAG A-3' (SEQ ID NO:12), and a second IS1001 probe provided in a kit of the invention can include the sequence 5'-GCT GGA CAA GGC TCG-3' (SEQ ID NO:13).

Articles of manufacture can include fluorophoric moieties for labeling the probes or probes already labeled with donor and corresponding acceptor fluorescent moieties. The article of manufacture can also include a package insert having instructions thereon for using the primers, probes, and fluorophoric moieties to detect the presence or absence of *Bordetella* in a biological sample and can further include instructions thereon for using the probes to distinguish between *B. pertussis* and/or *B. parapertussis* in a biological sample.

In yet another aspect of the invention, there is provided a method for detecting the presence or absence of *B. pertussis* in a biological sample from an individual. Such a method includes performing at least one cycling step. A cycling step can include an amplifying step and a hybridizing step. Generally, an amplifying step includes contacting the sample with a pair of IS481 primers to produce an IS481 amplification product if a *B. pertussis* IS481 nucleic acid molecule is present in the sample. Generally, a hybridizing step includes contacting the sample with an IS481 probe. Such an IS481 probe is usually labeled with a donor fluorescent moiety and a corresponding acceptor fluorescent moiety. The methods further include detecting the presence or absence of fluorescence resonance energy transfer (FRET) between the donor fluorescent moiety and the acceptor fluorescent moiety of the IS481 probe. The presence or absence of FRET is indicative of the presence or absence of *B. pertussis* in said sample. In addition to the IS481 primers and probe described herein, this method also can be performed using IS1001 primers and probe.

In one aspect, amplification can employ a polymerase enzyme having 5' to 3' exonuclease activity. Thus, the donor and acceptor fluorescent moieties would be within no more than 5 nucleotides of each other along the length of the probe. In another aspect, the IS481 probe includes a nucleic acid sequence that permits secondary structure formation. Such secondary structure formation generally results in spatial proximity between the donor and corresponding acceptor fluorescent moiety. According to this method, the acceptor fluorescent moiety on a probe can be a quencher.

In another aspect of the invention, there is provided a method for detecting the presence or absence of *B. pertussis* in a biological sample from an individual. Such a method includes performing at least one cycling step. A cycling step can include an amplifying step and a dye-binding step. An amplifying step generally includes contacting the sample with a pair of IS481 primers to produce an IS481 amplification product if a *B. pertussis* IS481 nucleic acid molecule is present in the sample. A dye-binding step generally includes contacting the IS481 amplification product with a nucleic acid binding dye. The method further includes detecting the presence or absence of binding of the nucleic acid binding dye to the amplification product. According to the invention, the presence of binding is typically indicative of the presence of *B. pertussis* in the sample, and the absence of binding is typically indicative of the absence of *B. pertussis* in the sample. Such a method can further include the steps of determining the melting temperature between the IS481 amplification product and the nucleic acid binding dye. Generally, the melting temperature confirms the presence or absence of

*B. pertussis*. Representative double-stranded DNA binding dyes include SYBRGreenI®, SYBRGold®, and ethidium bromide.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

DETAILED DESCRIPTION

*B. pertussis*, the bacterium causing pertussis or "whooping cough" has traditionally been difficult to detect in a clinically useful manner. Several diagnostic methods are available, but most lack sensitivity, require extended culture incubation times for results, and/or require repeated sampling and testing to verify significant increases of immunoglobulin G antibodies against pertussis toxin or immunoglobulin A antibodies against *B. pertussis* in paired sera. The present invention provides methods of detecting *B. pertussis* and/or *B. parapertussis* in a biological sample from an individual suspected of having pertussis. The methods feature the ability to distinguish between *B. pertussis* and *B. parapertussis*. The invention further provides kits containing primers and probes to carry out the differential diagnostic methods of the invention.
Pertussis

*B. pertussis* is transmitted by respiratory droplets and causes disease only in humans. Virulence factors of *B. pertussis* include agglutinogens, fimbriae, P.69/pertactin, pertussis toxin, filamentous haemagglutinin, adenylate cyclase, tracheal cytotoxin, dermonecrotic toxin, lipopolysaccharide, tracheal colonization factor, serum resistance factor, and type III secretion. Virulence factor expression is regulated by the bvgAS locus, a two-component signal transduction system. The pathophysiological sequence consists of attachment (fimbriae, P.69/pertactin, tracheal colonization factor, pertussis toxin, filamentous haemagglutinin), evasion of host defense (adenylate cyclase, petussis toxin, serum resistance factor), local effects (tracheal cytotoxin), and systemic effects (pertussis toxin).

Various methods to diagnose pertussis are available, including culture, serological methods, and the polymerase chain reaction (PCR). Serotyping of isolates to detect agglutinogens 2 and 3 is useful because serotype 1,2 may be associated with higher mortality, and antibodies to the agglutinins may be protective in both animals and humans. Acellular vaccines containing one to five components are increasingly being used in various countries. Immunization using whole-cell vaccine is also effective but is reactogenic. Protective immunity to pertussis correlates with high levels of antibody to each of pertactin, fimbriae, and pertussis toxin.

Pertussis is a communicable disease that can be very severe in young infants. Early diagnosis and treatment are essential to limit the severity of the disease and minimize transmission. The wide prevalence of pertussis and its changing epidemiology has highlighted the need for more sensitive and rapid methods for diagnostic testing. Current diagnostic tests for *B. pertussis* and *B. parapertussis* are difficult to perform due to the fastidious nature of *Bordetella* organisms, lack sensitivity, and require 3-5 days of growth to allow identification. Serologic testing by enzyme-linked immunosorbent assay (ELISA) or Western blot is sensitive and specific, but requires the comparison of 2 serum specimens from the subject collected over a 4-week interval. Direct fluorescent antibody testing (DFA) of nasopharyngeal secretions lacks sensitivity. The reference method is direct culture of the organism from nasopharyngeal secretions, but direct culture of *Bordetella* has a turnaround time of 1 to 2 days. Further, the organism is susceptible to environmental exposure (changes in temperature and drying) and has specific growth requirements, making recovery by culture difficult.

*B. pertussis* and *B. parapertussis* Nucleic Acids and Oligonucleotides

In one embodiment, methods of the invention use the insertion sequence IS481 (GenBank Accession No. M28220; SEQ ID NO:9) to detect *B. pertussis* in a biological sample. *B. pertussis* typically contains 50-100 copies of IS481. The IS481 sequence was described by McPheat et al. (*J. Gen. Microbiol.*, 135:1515-1520, 1989). In another embodiment, methods of the invention use the insertion sequence IS1001 (GenBank Accession No. X66858; SEQ ID NO:10) to detect *B. parapertussis* in a biological sample. *B. parapertussis* typically contains 30-35 copies of IS1001. The IS1001 sequence was described by van der Zee et al. (*J. Bacteriol.*, 175:141-147, 1993). *Bordetella* nucleic acids other than those exemplified herein (e.g., other than IS481 or IS1001 nucleic acids) also can be used to detect *Bordetella* in a sample and are known to those of skill in the art. Specifically, primers and probes to amplify and detect *B. pertussis* IS481 nucleic acid are provided by the invention, as are primers and probes to amplify and detect *B. parapertussis* IS1001 nucleic acid.

Primers that amplify a *Bordetella* nucleic acid molecule (e.g., IS481 or IS1001) can be designed using, for example, a computer program such as OLIGO (Molecular Biology Insights, Inc., Cascade, Colo.). Important features when designing oligonucleotides to be used as amplification primers include, but are not limited to, an appropriate size amplification product to facilitate detection (e.g., by electrophoresis), similar melting temperatures for the members of a pair of primers, and the length of each primer (i.e., the primers need to be long enough to anneal with sequence-specificity and to initiate synthesis but not so long that fidelity is reduced during oligonucleotide synthesis). Typically, oligonucleotide primers are 8 to 50 nucleotides in length (e.g., 10, 12, 14, 16, 18, 20, 22, 24, 26, 28, 30, 32, 34, 36, 38, 40, 42, 44, 46, 48, or 50 nucleotides in length). "IS481 primers" and "IS1001 primers" as used herein refers to oligonucleotide primers that specifically anneal to *B. pertussis* IS481 nucleic acid sequences and *B. parapertussis* IS1001 nucleic acid sequences, respectively, and initiate synthesis therefrom under appropriate conditions.

Designing oligonucleotides to be used as hybridization probes can be performed in a manner similar to the design of primers, although the members of a pair of probes preferably anneal to an amplification product within no more than 5 nucleotides of each other on the same strand such that FRET can occur (e.g., within no more than 1, 2, 3, or 4 nucleotides of each other). This minimal degree of separation typically brings the respective fluorescent moieties into sufficient proximity such that FRET can occur. It is to be understood, however, that other separation distances (e.g., 6 or more nucleotides) are possible provided the fluorescent moieties are appropriately positioned relative to each other (for example, with a linker arm) such that FRET can occur. In addition, probes can be designed to hybridize to targets that contain a mutation or polymorphism, thereby allowing differential detection based on either absolute hybridization of different pairs of probes corresponding to the particular species to be distinguished or differential melting temperatures between, for example, members of a pair of probes and each amplification product corresponding to the species to be distinguished. As with oligonucleotide primers, oligonucleotide probes usually have similar melting temperatures, and the length of each probe must be sufficient for sequence-specific hybridization to occur but not so long that fidelity is reduced during synthesis. Oligonucleotide probes are 8 to 50 nucleotides in length (e.g., 10, 12, 14, 16, 18, 20, 22, 24, 26, 28, 30, 32, 34, 36, 38, 40, 42, 44, 46, 48, or 50 nucleotides in length). "IS481 probes" and "IS1001 probes" as used herein refers to oligonucleotide probes that specifically anneal to a *B. pertussis* IS481 amplification product and a *B. parapertussis* IS1001 amplification product, respectively.

Constructs of the invention include vectors containing a *Bordetella* nucleic acid e.g., an IS481 or IS1001 nucleic acid molecule, or fragment thereof. Constructs can be used, for example, as control template nucleic acid molecules. Vectors suitable for use in the present invention are commercially available and/or produced by recombinant DNA technology methods routine in the art. IS481 or IS1001 nucleic acid molecules can be obtained, for example, by chemical synthesis, direct cloning from the respective *Bordetella* organism, or by PCR amplification. Constructs suitable for use in the methods of the invention typically include, in addition to IS481 or IS1001 nucleic acid molecules, sequences encoding a selectable marker (e.g., an antibiotic resistance gene) for selecting desired constructs and/or transformants, and an origin of replication. The choice of vector systems usually depends upon several factors, including, but not limited to, the choice of host cells, replication efficiency, selectability, inducibility, and the ease of recovery.

Constructs of the invention containing IS481 or IS1001 nucleic acid molecules can be propagated in a host cell. As used herein, the term host cell is meant to include prokaryotes and eukaryotes such as yeast, plant and animal cells. Prokaryotic hosts may include *E. coli, Salmonella tymphimurium, Serratia marcescens* and *Bacillus subtilis*. Eukaryotic hosts include yeasts such as *S. cerevisiae, S. pombe, Pichia pastoris*, mammalian cells such as COS cells or Chinese hamster ovary (CHO) cells, insect cells, and plant cells such as *Arabidopsis thaliana* and *Nicotiana tabacum*. A construct of the invention can be introduced into a host cell using any of the techniques commonly known to those of ordinary skill in the art. For example, calcium phosphate precipitation, electroporation, heat shock, lipofection, microinjection, and viral-mediated nucleic acid transfer are common methods for introducing nucleic acids into host cells. In addition, naked DNA can be delivered directly to cells (see, e.g., U.S. Pat. Nos. 5,580,859 and 5,589,466).

Polymerase Chain Reaction (PCR)

U.S. Pat. Nos. 4,683,202, 4,683,195, 4,800,159, and 4,965,188 disclose conventional PCR techniques. PCR typically employs two oligonucleotide primers that bind to a selected nucleic acid template (e.g., DNA or RNA). Primers useful in the present invention include oligonucleotides capable of acting as a point of initiation of nucleic acid synthesis within IS481 or IS1001 nucleic acid sequences. A primer can be purified from a restriction digest by conventional methods, or it can be produced synthetically. The primer is preferably single-stranded for maximum efficiency in amplification, but the primer can be double-stranded. Double-stranded primers are first denatured, i.e., treated to separate the strands. One method of denaturing double-stranded nucleic acids is by heating.

The term "thermostable polymerase" refers to a polymerase enzyme that is heat stable, i.e., the enzyme catalyzes the formation of primer extension products complementary to a template and does not irreversibly denature when subjected to the elevated temperatures for the time necessary to effect denaturation of double-stranded template nucleic acids. Generally, the synthesis is initiated at the 3' end of each primer and proceeds in the 5' to 3' direction along the template strand. Thermostable polymerases have been isolated from *Thermus flavus, T. ruber, T. thermophilus, T. aquaticus, T. lacteus, T. rubens, Bacillus stearothermophilus*, and *Methanothermus fervidus*. Nonetheless, polymerases that are not thermostable also can be employed in PCR assays provided the enzyme is replenished.

If the *B. pertussis* or *B. parapertussis* template nucleic acid is double-stranded, it is necessary to separate the two strands before it can be used as a template in PCR. Strand separation can be accomplished by any suitable denaturing method including physical, chemical or enzymatic means. One method of separating the nucleic acid strands involves heating the nucleic acid until it is predominately denatured (e.g., greater than 50%, 60%, 70%, 80%, 90% or 95% denatured). The heating conditions necessary for denaturing template nucleic acid will depend, e.g., on the buffer salt concentration and the length and nucleotide composition of the nucleic acids being denatured, but typically range from about 90° C. to about 105° C. for a time depending on features of the reaction such as temperature and the nucleic acid length. Denaturation is typically performed for about 30 sec to 4 min.

If the double-stranded nucleic acid is denatured by heat, the reaction mixture is allowed to cool to a temperature that promotes annealing of each primer to its target sequence on the template nucleic acid. The temperature for annealing is usually from about 35° C. to about 65° C. Annealing times can be from about 10 secs to about 1 min. The reaction mixture is then adjusted to a temperature at which the activity of the polymerase is promoted or optimized, i.e., a temperature sufficient for extension to occur from the annealed primer to generate products complementary to the template nucleic acid. The temperature should be sufficient to synthesize an extension product from each primer that is annealed to a nucleic acid template, but should not be so high as to denature an extension product from its complementary template (e.g., the temperature for extension generally ranges from about 40° to 80° C.). Extension times can be from about 10 secs to about 5 mins.

PCR assays can employ template nucleic acid such as DNA or RNA, including messenger RNA (mRNA). The template nucleic acid need not be purified; it may be a minor fraction of a complex mixture, such as *B. pertussis* or *B. parapertussis* nucleic acid contained in human cells. DNA or RNA may be extracted from a biological sample such as nasopharyngeal swabs, nasopharyngeal aspirates, and throat swabs by routine techniques such as those described in *Diagnostic Molecular Microbiology: Principles and Applications* (Persing et al. (eds), 1993, American Society for Microbiology, Washington D.C.). Template nucleic acids can be obtained from any number of sources, such as plasmids, or natural sources including bacteria, yeast, viruses, organelles, or higher organisms such as plants or animals.

The oligonucleotide primers are combined with PCR reagents under reaction conditions that induce primer extension. For example, chain extension reactions generally include 50 mM KCl, 10 mM Tris-HCl (pH 8.3), 1.5 mM $MgCl_2$, 0.001% (w/v) gelatin, 0.5-1.0 µg denatured template DNA, 50 pmoles of each oligonucleotide primer, 2.5 U of Taq polymerase, and 10% DMSO). The reactions usually contain 150 to 320 µM each of dATP, dCTP, dTTP, dGTP, or one or more analogs thereof.

The newly synthesized strands form a double-stranded molecule that can be used in the succeeding steps of the reaction. The steps of strand separation, annealing, and elongation can be repeated as often as needed to produce the desired quantity of amplification products corresponding to the target nucleic acid molecule. The limiting factors in the reaction are the amounts of primers, thermostable enzyme, and nucleoside triphosphates present in the reaction. The cycling steps (i.e., denaturation, annealing, and extension) are preferably repeated at least once. For use in detection, the number of cycling steps will depend, e.g., on the nature of the sample. If the sample is a complex mixture of nucleic acids, more cycling steps will be required to amplify the target sequence sufficient for detection. Generally, the cycling steps are repeated at least about 20 times, but may be repeated as many as 40, 60, or even 100 times.

Fluorescent Resonance Energy Transfer (FRET)

FRET technology (see, for example, U.S. Pat. Nos. 4,996,143, 5,565,322, 5,849,489, and 6,162,603) is based on the concept that when a donor and a corresponding acceptor fluorescent moiety are positioned within a certain distance of each other, energy transfer takes place between the two fluorescent moieties that can be visualized or otherwise detected and/or quantitated. Two oligonucleotide probes, each containing a fluorescent moiety, can hybridize to an amplification product at particular positions determined by the complementarity of the oligonucleotide probes to the target nucleic acid sequence. Upon hybridization of the oligonucleotide probe to the amplification product at the appropriate positions, a FRET signal is generated. Hybridization temperatures can range from about 35° C. to about 65° C. for about 10 seconds to about 1 minute.

Fluorescent analysis can be carried out using, for example, a photon counting epifluorescent microscope system (containing the appropriate dichroic mirror and filters for monitoring fluorescent emission at the particular range), a photon counting photomultiplier system or a fluorometer. Excitation to initiate energy transfer can be carried out with an argon ion laser, a high intensity mercury (Hg) arc lamp, a fiber optic light source, or other high intensity light source appropriately filtered for excitation in the desired range.

As used herein with respect to donor and corresponding acceptor fluorescent moieties, "corresponding" refers to an acceptor fluorescent moiety having an emission spectrum that overlaps the excitation spectrum of the donor fluorescent moiety. The wavelength maximum of the emission spectrum of the acceptor fluorescent moiety should be at least 100 nm greater than the wavelength maximum of the excitation spectrum of the donor fluorescent moiety. Accordingly, efficient non-radiative energy transfer can be produced therebetween.

Fluorescent donor and corresponding acceptor moieties are generally chosen for (a) high efficiency Förster energy transfer; (b) a large final Stokes shift (>100 nm); (c) shift of the emission as far as possible into the red portion of the visible spectrum (>600 nm); and (d) shift of the emission to a higher wavelength than the Raman water fluorescent emission produced by excitation at the donor excitation wavelength. For example, a donor fluorescent moiety can be chosen that has its excitation maximum near a laser line (for example, Helium-Cadmium 442 nm or Argon 488 nm), a high extinction coefficient, a high quantum yield, and a good overlap of its fluorescent emission with the excitation spectrum of the corresponding acceptor fluorescent moiety. A corresponding acceptor fluorescent moiety can be chosen that has a high extinction coefficient, a high quantum yield, a good overlap of its excitation with the emission of the donor fluorescent moiety, and emission in the red part of the visible spectrum (>600 nm).

Representative donor fluorescent moieties that can be used with various acceptor fluorescent moieties in FRET technology include fluorescein, Lucifer Yellow, B-phycoerythrin, 9-acridineisothiocyanate, Lucifer Yellow VS, 4-acetamido-4'-isothiocyanatostilbene-2,2'-disulfonic acid, 7-diethylamino-3-(4'-isothiocyanatophenyl)-4-methylcoumarin, succinimdyl 1-pyrenebutyrate, and 4-acetamido-4'-isothiocyanatostilbene-2,2'-disulfonic acid derivatives. Representative acceptor fluorescent moieties, depending upon the donor fluorescent moiety used, include LCT™-Red 640, LC™-Red 705, Cy5, Cy5.5, Lissamine rhodamine B sulfonyl chloride, tetramethyl rhodamine isothiocyanate, rhodamine x isothiocyanate, erythrosine isothiocyanate, fluorescein, diethylenetriamine pentaacetate or other chelates of Lanthanide ions (e.g., Europium, or Terbium). Donor and acceptor fluorescent moieties can be obtained, for example, from Molecular Probes (Junction City, Oreg.) or Sigma Chemical Co. (St. Louis, Mo.).

The donor and acceptor fluorescent moieties can be attached to the appropriate probe oligonucleotide via a linker arm. The length of the linker arm is important, as the linker arms will affect the distance between the donor and acceptor fluorescent moieties. The length of a linker arm for the purpose of the present invention is the distance in Angstroms (Å) from the nucleotide base to the fluorescent moiety. In general, a linker arm is from about 10 to about 25 Å. The linker arm may be of the kind described in WO 84/03285. WO 84/03285 also discloses methods for attaching linker arms to a particular nucleotide base, and also for attaching fluorescent moieties to a linker arm.

An acceptor fluorescent moiety such as an LCT™-Red 640-NHS-ester can be combined with C6-Phosphoramidites (available from ABI (Foster City, Calif.) or Glen Research (Sterling, Va.)) to produce, for example, LC-Red 640-Phosphoramidite. Frequently used linkers to couple a donor fluorescent moiety such as fluorescein to an oligonucleotide include thiourea linkers (FITC-derived, for example, fluorescein-CPG's from Glen Research or ChemGene (Ashland, Mass.)), amide-linkers (fluorescein-NHS-ester-derived, such as fluorescein-CPG from BioGenex (San Ramon, Calif.)), or 3'-amino-CPG's that require coupling of a fluorescein-NHS-ester after oligonucleotide synthesis.

Detection of *B. pertussis* and/or *B. parapertussis*

The present invention provides methods for detecting the presence or absence of *B. pertussis* and/or *B. parapertussis* in a biological sample from an individual. The methods include performing at least one cycling step that first includes contacting the sample with a pair of IS481 and/or IS1001 primers to produce an IS481 amplification product if *B. pertussis* is present in the sample, and/or an IS1001 amplification product if *B. parapertussis* is present in the sample. Each of the IS481 or IS1001 primers anneals to a target within or adjacent to a IS481 or IS1001 nucleic acid molecule, respectively, such that at least a portion of each amplification product contains nucleic acid sequence corresponding to IS481 or IS1001, respectively. More importantly, the amplification product should contain the nucleic acid sequences that are complementary to the IS481 or IS1001 probes, respectively. Each cycling step further includes contacting the sample with a pair of IS481 and/or IS1001 probes. According to the invention, one member of each pair of the IS481 and IS1001 probes is labeled with a donor fluorescent moiety and the other is labeled with a corresponding acceptor fluorescent moiety. The presence or absence of FRET between the donor fluorescent moiety of the first IS481 or IS1001 probe and the corresponding acceptor fluorescent moiety of the second IS481 or IS1001 probe, respectively, is detected upon hybridization of the probes to the respective amplification product. Multiple cycles of amplification and hybridization are performed, preferably in a thermocycler.

The methods of the invention can be performed individually to detect either *B. pertussis* or *B. parapertussis*, but combining the primers and probes in a single assay to detect the repetitive insertion molecules (IS481/IS1001) of *B. pertussis* and *B. parapertussis* provides a rapid and sensitive test that can distinguish between the species in a single reaction. Representative biological samples that can be used in practicing the methods of the invention include nasopharyngeal swabs, nasopharyngeal aspirates, throat swabs, or any biological specimen or swab containing ciliated respiratory epithelium that has the potential to harbor *Bordetella* species. Biological samples are generally processed (e.g., by nucleic acid extraction methods known in the art) to release *Bordetella* nucleic acid.

As used herein, "amplifying" refers to the process of synthesizing nucleic acid molecules that are complementary to one or both strands of a template nucleic acid molecule (e.g., IS481 or IS1001 nucleic acid molecules). Amplifying a nucleic acid molecule typically includes denaturing the template nucleic acid, annealing primers to the template nucleic acid at a temperature that is below the melting temperatures of the primers, and enzymatically elongating from the primers to generate an amplification product. Amplification typically requires the presence of deoxyribonucleoside triphosphates, a DNA polymerase enzyme (e.g., Platinum® Taq) and an appropriate buffer and/or co-factors for optimal activity of the polymerase enzyme (e.g., $MgCl_2$ and/or KCl).

If amplification of *Bordetella* nucleic acid occurs and an amplification product is produced, the step of hybridizing results in a detectable signal based upon FRET between the members of the pair of probes. As used herein, "hybridizing" refers to the annealing of probes to an amplification product. Hybridization conditions typically include a temperature that is below the melting temperature of the probes but that avoids non-specific hybridization of the probes.

Melting curve analysis is an additional step that can be included in a cycling profile. Melting curve analysis is based on the fact that DNA melts at a characteristic temperature called the melting temperature (Tm), which is defined as the temperature at which half of the DNA duplexes have separated into single strands. The melting temperature of a DNA depends primarily upon its nucleotide composition. Thus, DNA molecules rich in G and C nucleotides have a higher Tm than those having an abundance of A and T nucleotides. By detecting the temperature at which signal is lost, the melting temperature of probes can be determined. Similarly, by detecting the temperature at which signal is generated, the annealing temperature of probes can be determined. The melting temperature(s) of the IS481 and IS1001 probes from the respective amplification product(s) can confirm the presence or absence of *B. pertussis* and *B. parapertussis* in the sample, and can distinguish between *B. pertussis* and *B. parapertussis*. Alternatively, a Lightcycler™ apparatus allows for multiple wavelengths to be measured simultaneously. Therefore, the second IS481 and IS1001 probe can be labeled with different acceptor fluorescent moieties (e.g., LC-Red 640 and LC-Red 705), thereby providing a method of distinguishing between *B. pertussis* and *B. parapertussis* based on differential FRET signals.

Generally, the presence of FRET indicates the presence of *B. pertussis* and/or *B. parapertussis* in the biological sample, and the absence of FRET indicates the absence of *B. pertussis* and *B. parapertussis* in the biological sample. Using the methods disclosed herein, detection of FRET within 40 cycles (e.g., within 30, 25, or 20 cycles) is indicative of a *B. pertussis* and/or *B. parapertussis* infection. A positive result indicates the presence of nucleic acid from *B. pertussis* and/or *B. parapertussis* in the biological sample. In some cases, a positive result will be positive for both *B. pertussis* and *B. parapertussis*. A negative result indicates the absence of detectable DNA in the specimen submitted for analysis, but does not negate the possibility of the organism's presence in very small quantities. A negative result can occur when inhibitory substances are present in the specimen (studies herein have demonstrated 14% of nasopharyngeal specimens contain unknown PCR-inhibitory components). Inadequate specimen collection, transportation delays, inappropriate transportation conditions, or use of certain collection swabs (calcium alginate or aluminum shaft) are all conditions that can affect the success and/or accuracy of the test result.

Methods of the invention also can be used for vaccine efficacy studies or epidemiology studies of either or both *B. pertussis* and *B. parapertussis*. For example, an attenuated *B. pertussis* or *B. parapertussis* in a vaccine can be detected using the methods of the invention during the time when bacteria is still present in an individual. For such vaccine efficacy studies, the methods of the invention can be used to determine, for example, the persistence of an attenuated strain of *B. pertussis* or *B. parapertussis* used in a vaccine, or can be performed in conjunction with an additional assay such as a serologic assay to monitor an individual's immune response to such a vaccine. In addition, methods of the invention can be used to distinguish one *B. pertussis* or *B. parapertussis* strain from another for epidemiology studies of, for example, the origin or severity of an outbreak of *B. pertussis* or *B. parapertussis*, respectively.

Methods of the invention are highly sensitive and highly specific. The real-time PCR method disclosed herein is far more sensitive than culture and DFA and superior to the conventional PCR due to the ability to differentiate between two species of *Bordetella*. The methods of the invention do not require gel electrophoresis or Southern hybridization, making the methods described herein much more rapid than any *Bordetella* detection method currently available. Rapid diagnosis leading to treatment with antibiotics can prevent potentially serious consequences from *Bordetella* respiratory infections.

Within each thermocycler run, control samples are cycled as well. Positive control samples can amplify *Bordetella* nucleic acid control template (other than the IS481 or IS1001 nucleic acid) using, for example, control primers and control probes. Positive control samples can also amplify, for example, a plasmid construct containing IS481 and/or IS1001. Such a plasmid control can be amplified internally (e.g., within each sample) or in a separate sample run side-by-side with the patients' samples. The use of such controls can identify false-negatives due, for example, to the inhibition of PCR observed with some samples. Each thermocycler run should also include a negative control that, for example, lacks template DNA.

In an embodiment, the methods of the invention include steps to avoid contamination. For example, an enzymatic method utilizing uracil-DNA glycosylase is described in U.S. Pat. Nos. 5,035,996, 5,683,896 and 5,945,313 to reduce or eliminate contamination between one thermocycler run and the next. In addition, standard laboratory containment practices and procedures are desirable when performing methods of the invention. Containment practices and procedures include, but are not limited to, separate work areas for different steps of a method, containment hoods, barrier filter pipette tips and dedicated air displacement pipettes. Consistent containment practices and procedures by personnel are necessary for accuracy in a diagnostic laboratory handling clinical samples.

Conventional PCR methods in conjunction with FRET technology can be used to practice the methods of the invention. In one embodiment, a LightCycler™ instrument is used. A detailed description of the LightCycler™ System and real-time and on-line monitoring of PCR can be found at http://biochem.roche.com/lightcycler. The following patent applications describe real-time PCR as used in the LightCycler™ technology: WO 97/46707, WO 97/46714 and WO 97/46712. The LightCycler™ instrument is a rapid thermocycler combined with a microvolume fluorometer utilizing high quality optics. This rapid thermocycling technique uses thin glass cuvettes as reaction vessels. Heating and cooling of the reaction chamber are controlled by alternating heated and ambient air. Due to the low mass of air and the high ratio of surface area to volume of the cuvettes, very rapid temperature exchange rates can be achieved within the LightCycler™ thermal chamber. Addition of selected fluorescent dyes to the reaction components allows the PCR to be monitored in real-time and on-line. Furthermore, the cuvettes serve as an optical element for signal collection (similar to glass fiber optics), concentrating the signal at the tip of the cuvettes. The effect is efficient illumination and fluorescent monitoring of microvolume samples.

The LightCycler™ carousel that houses the cuvettes can be removed from the instrument. Therefore, samples can be loaded outside of the instrument (in a PCR Clean Room, for example). In addition, this feature allows for the sample carousel to be easily cleaned and sterilized. The fluorimeter, as part of the LightCycler™ apparatus, houses the light source. The emitted light is filtered and focused by an epi-illumination lens onto the top of the cuvettes. Fluorescent light emitted from the sample is then focused by the same lens, passed through a dichroic mirror, filtered appropriately, and focused onto data-collecting photohybrids. The optical unit currently available in the LightCycler™ instrument (Roche Molecular Biochemicals, Catalog No. 2 011 468) includes three band-pass filters (530 nm, 640 nm, and 710 nm), providing three-color detection and several fluorescence acquisition options. Data collection options include once per cycling step monitoring, fully continuous single-sample acquisition for melting curve analysis, continuous sampling (in which sampling frequency is dependent on sample number) and/or stepwise measurement of all samples after defined temperature interval.

The LightCycler™ can be operated using a PC workstation and can utilize a Windows NT operating system. Signals from the samples are obtained as the machine positions the cuvettes sequentially over the optical unit. The software can display the fluorescence signals in real-time immediately after each measurement. Fluorescent acquisition time is 10-100 milliseconds (msec). After each cycling step, a quantitative display of fluorescence vs. cycle number can be continually updated for all samples. The data generated can be stored for further analysis.

A common FRET technology format utilizes two hybridization probes. Each probe can be labeled with a different fluorescent moiety and are generally designed to hybridize in close proximity to each other in a target DNA molecule (e.g., an amplification product). A donor fluorescent moiety, for example, fluorescein, is excited at 470 nm by the light source of the LightCycler™ Instrument. During FRET, the fluorescein transfers its energy to an acceptor fluorescent moiety such as LightCycler™-Red 640 (LC™-Red 640) or LightCycler™-Red 705 (LC™-Red 705). The acceptor fluorescent moiety then emits light of a longer wavelength, which is detected by the optical detection system of the LightCycler™ instrument. Efficient FRET can only take place when the fluorescent moieties are in direct local proximity and when the emission spectrum of the donor fluorescent moiety overlaps with the absorption spectrum of the acceptor fluorescent moiety. The intensity of the emitted signal can be correlated with the number of original target DNA molecules (e.g., the number of *B. pertussis* or *B. parapertussis* organisms).

Another FRET technology format utilizes TaqMan® technology to detect the presence or absence of an amplification product, and hence, the presence or absence of *B. pertussis* or *B. parapertussis*. TaqMan® technology utilizes one single-stranded hybridization probe labeled with two fluorescent moieties. When a first fluorescent moiety is excited with light of a suitable wavelength, the absorbed energy is transferred to a second fluorescent moiety according to the principles of FRET. The second fluorescent moiety is generally a quencher molecule. During the annealing step of the PCR reaction, the labeled hybridization probe binds to the target DNA (i.e., the amplification product) and is degraded by the 5' to 3' exonuclease activity of the Taq Polymerase during the subsequent elongation phase. As a result, the excited fluorescent moiety and the quencher moiety become spatially separated from one another. As a consequence, upon excitation of the first fluorescent moiety in the absence of the quencher, the fluorescence emission from the first fluorescent moiety can be detected. By way of example, an ABI PRISM® 7700 Sequence Detection System (Applied Biosystems, Foster City, Calif.) uses TaqMan® technology, and is suitable for performing the methods described herein for detecting *Bordetella*. Information on PCR amplification and detection using an ABI PRISM® 770 system can be found at http://www.appliedbiosystems.com/products.

Yet another FRET technology format utilizes molecular beacon technology to detect the presence or absence of an amplification product, and hence, the presence or absence of *Bordetella*. Molecular beacon technology uses a hybridization probe labeled with a donor fluorescent moiety and an acceptor fluorescent moiety. The acceptor fluorescent moiety is generally a quencher, and the fluorescent labels are typically located at each end of the probe. Molecular beacon technology uses a probe oligonucleotide having sequences that permit secondary structure formation (e.g., a hairpin). As a result of secondary structure formation within the probe, both fluorescent moieties are in spatial proximity when the probe is in solution. After hybridization to the target nucleic acids (i.e., amplification products), the secondary structure of the probe is disrupted and the fluorescent moieties become separated from one another such that after excitation with light of a suitable wavelength, the emission of the first fluorescent moiety can be detected.

As an alternative to detection using FRET technology, an amplification product can be detected using a nucleic acid binding dye such as a fluorescent DNA binding dye (e.g., SYBRGreenI® or SYBRGold® (Molecular Probes)). Upon interaction with the double-stranded nucleic acid, such nucleic acid binding dyes emit a fluorescence signal after excitation with light at a suitable wavelength. A nucleic acid binding dye such as a nucleic acid intercalating dye also can be used. When nucleic acid binding dyes are used, a melting curve analysis is usually performed for confirmation of the presence of the amplification product.

It is understood that the present invention is not limited by the configuration of one or more commercially available instruments.

Articles of Manufacture

The invention further provides for articles of manufacture to detect *B. pertussis* and/or *B. parapertussis*. An article of manufacture according to the present invention can include primers and probes used to detect *B. pertussis* or *B. parapertussis*, together with suitable packaging materials. Representative primers and probes for detection of *B. pertussis* are capable of hybridizing to IS481 nucleic acid molecules. Representative primers and probes for detection of *B. parapertussis* are capable of hybridizing to IS1001 nucleic acid molecules. Methods of designing primers and probes are disclosed herein, and representative examples of primers and probes that amplify and differentially detect to *B. pertussis* and *B. parapertussis* nucleic acid molecules are provided herein.

Articles of manufacture of the invention can also include one or more fluorescent moieties for labeling the probes or, alternatively, the probes supplied with the kit can be labeled. For example, an article of manufacture may include a donor fluorescent moiety for labeling one of the IS481 or IS1001 probes and a corresponding acceptor fluorescent moiety for labeling the other IS481 or IS1001 probe, respectively. Examples of suitable FRET donor fluorescent moieties and corresponding acceptor fluorescent moieties are provided herein.

Articles of manufacture of the invention also can contain a package insert or package label having instructions thereon for using the IS481 primers and probes to detect the presence or absence of *B. pertussis* in a biological sample and, likewise, using the IS1001 primers and probes to detect the presence or absence of *B. parapertussis* in a sample. Such a package insert may further contain instructions thereon for using IS481 and IS1001 probes to distinguish between *B. pertussis* and *B. parapertussis* within the same biological sample. Articles of manufacture may additionally include reagents for carrying out the methods disclosed herein (e.g., buffers, polymerase enzymes, co-factors, or agents to prevent contamination). Such reagents may be specific for one of the commercially available instruments described herein.

The invention will be further described in the following examples, which do not limit the scope of the invention described in the claims.

EXAMPLES

Example 1

DNA Extraction and *Bordetella* LightCycler™ Assay #1

Recovery of *Bordetella* from nasopharyngeal swabs was achieved by swabbing the nasopharynx with a nylon swab having an aluminum shaft and transported in media. Upon arrival at Mayo, the swab was placed in 500 μl Sample Buffer (Reagent A) in a 1.5 ml microcentrifuge tube and stored at 2-8° C. 200 μl of the specimen in Sample Buffer was used for DNA extraction and the remainder was saved at −70° C. for future use. Sample Buffer was added to nasopharyngeal aspirates to bring the volume up to 500 μl.

The DNA sample was taken into a 'PCR Set-Up Room' and 200 μl of the sample was transferred into 2.0 ml microcentrifuge tubes. DNA extraction was performed in an 'Extraction PCR Workstation' using an Isoquick DNA Extraction Kit (ORCA Research, Inc.; Bothell, Wash.; Catalog #217539). Pellet Paint™ NF Co-Precipitant (Novagen; Madison, Wis.; Catalog #70748-3) was used in all extractions. For diagnostic labs running multiple tests on the same biological sample, refer to 'Nucleic Acid Procedures Shared among Molecular Microbiology Tests' provided with the Isoquick DNA Extraction kit.

Alternatively, DNA was prepared from a sample by boiling and centrifugation. Briefly, the swab was rinsed with 200 μl of water that was collected in a 2 ml screw cap tube. The tube was centrifuged at 13,000×g for 1 min and the supernatant was removed. The pellet was resuspended in 100 μl of RNase-free water and boiled at 100° C. for 10 min. The tube was centrifuged at 13,000×g for 1 min and the supernatant collected.

In a 'PCR Clean Room', the frozen *B. pertussis* and *B. parapertussis* LightCycler™ PCR master-mixes were thawed, vortexed briefly and centrifuged for 1 minute at 20,800×g. If prepared separately, the *B. pertussis* and *B. parapertussis* master mixes were combined 1:1 in a 1.5 ml Eppendorf tube and mixed. The amount of time the reagents were left at room temperature was minimized. The LightCycler™ carousel was loaded with two cuvettes representing positive controls, an appropriate number of negative controls, and the remainder with patient's samples. 15 μl of the combined *Bordetella* PCR master-mix was added to each cuvette using a repeat pipettor.

The cuvettes containing the *Bordetella* PCR master-mix were transferred to a 'Target Loading PCR Workstation' and 5 μl of the sample supernatant was carefully removed and added to the 15 μl of *Bordetella* PCR master-mix in each LightCycler™ cuvette. The cuvettes were capped. The carousel was transported to a lightCycler™ Area' and was centrifuged in the LightCycler™ carousel centrifuge. The carousel was placed in the LightCycler™ apparatus and the *Bordetella* LightCycler™ program was run. Samples underwent 40 cycles of: denaturation at about 95° C. immediately followed by primers annealing to the template nucleic acid for about 20 secs at about 60° C., and elongation of the newly-synthesized strands at about 72° C. for about 14 secs. During the run, the specimen names were entered and typed into the LightCycler™ software sample table. The run was complete in about one hour.

After completion of the run, the cuvettes were removed from the carousel with a cuvette extruder or by turning the carousel upside down and gently loosening the cuvettes until they fell into a collection bucket. The carousel was decontaminated in DNA-OFF (Daigger; Vernon Hills, Ill.; Cat. #HX12982) for 1 min, rinsed with de-ionized water and air dried before being returned to the 'PCR Clean Room'.

Extreme care was taken to avoid all contact of sample or sample extracts containing *Bordetella* DNA with any solutions or portion of the LightCycler™ apparatus prior to PCR amplification. False-positive reactions can occur due to cross-contamination from *Bordetella*-containing samples. For these reasons, the use of at least three separate areas for sample preparation and LightCycler™ setup are recommended: an area for PCR mix preparation (e.g., a 'PCR Clean Room'), an area for specimen processing and setting-up the PCR reactions (e.g., an 'Extraction PCR Workstation' or a 'Target Loading PCR Workstation'), and an area dedicated to the actual amplification reactions (e.g., a lightCycler™ Area'). Dedicated pipettes and barrier filter pipette tips can be used with all air displacement pipettes and careful pipetting can minimize any cross-contamination events.

Example 2

Primers and Probes

Primers (0.2 µM medium scale synthesis) were ordered from the Mayo Molecular Biology Core Facility (Rochester, Minn.). Primers were dried down at 60° C. with vacuum (22 psi), and resuspended in 500 µl to 1 ml RNase-free water. Primers were adjusted to 50 µM by measuring the $A_{260}$ of a 1/100 dilution (198 µl water+2 µl, DF=100). The concentration was estimated by the following formula: [DF×$A_{260}$×100/number of bases=µM]. The concentration was adjusted to 50 µM by adding water using the following formula: [((µM found/50)×µl remaining)−µl remaining=water to add]. Primers were mixed (1:1) to make a stock solution containing 25 µM of each primer and stored at −20° C.

Probes were obtained from Idaho Technologies (http://www.idahotech.comd/itbiochem/index.html). The probes were suspended in 1×TE buffer supplied with the probes to a final concentration of 20 µM.

The $A_{260}$ and $A_{494}$ of the fluorescein-labeled probe were measured. The extinction coefficient ($e_{260}$) of the fluorescein-labeled probe was calculated using nearest neighbor values. The LightCycler™ Probe QC, an Excel spreadsheet, was used to calculate the extinction coefficients and ratios.

The dye-oligonucleotide ratio was determined. The ratio should be between 0.8 and 1.2, which indicates that there is one dye molecule present for every oligonucleotide molecule. Probes were diluted 1/20 in 0.5×TE buffer (pH 8.3) to determine this ratio. The extinction coefficient of fluorescein is very sensitive to pH. [Dye µM=($A_{494}$/68,000)]. [Oligo µM=[$A_{260}$−($A_{494}$×12,000/68,000)]/$e_{260}$×DF×$10^6$].

The $A_{260}$ and $A_{622}$ of the LC-Red 640-labeled oligonucleotide were measured and the predicted extinction coefficient ($e_{260}$) was calculated using nearest neighbor values. [Dye µM=($A_{622}$/110,000)]. [Oligo µM=[$A_{260}$−($A_{622}$×31,000/110,000)]/$e_{260}$×DF×$10^6$].

TABLE 1

Primers and probes for detection of B. pertussis

| Type | Product Size (bp) | Name | Sequences (5'→3') | SEQ ID NO: |
|---|---|---|---|---|
| Primer | 234 | BP IS694 | ccagttcctcaaggacgc | 1 |
| Primer | 234 | BP IS905 | gagttctggtaggtgtgagcgta | 2 |
| Probe | | BP IS F | caccgctttacccgaccttaccgcccac | 3 |
| Probe | | BP IS R | gaccaatggcaaggccgaacgcttcatc | 4 |

F = fluorescein-labeled probe oligonucleotide; R = LC-Red 640-labeled probe oligonucleotide

TABLE 2

Primers and probes for detection of B. parapertussis

| Type | Product Size (bp) | Name | Sequences (5'→3') | SEQ ID NO: |
|---|---|---|---|---|
| Primer | 200 | BPP A375 | ggcgatatcaacgggtga | 5 |
| Primer | 200 | BPP A556 | cagggcaaactcgtccatc | 6 |
| Probe | | BPP F | gttcttcgaactgggttggcatac | 7 |
| Probe | | BPP R | gtcaagacgctggacaaggctc | 8 |

F = fluorescein-labeled probe oligonucleotide; R = LC-Red 640-labeled probe oligonucleotide Example 3

Bordetella LightCycler™ Assay #1

LightCycler™ PCR master-mixes were prepared in the 'PCR Clean Room'. This room was designed with positive airflow and is operated to minimize contamination with nucleic acid from specimens or positive controls. Disposable gowns and gloves were worn at all times.

LightCycler™ PCR mix was prepared according to the following chart. B. pertussis IS481 PCR mix and B. parapertussis IS1001 PCR mix were aliquoted into separate 2.0 ml screw-capped microcentrifuge tubes and stored at −70° C. for up to 6 mo. All reagents were thawed, gently vortexed and quick spun prior to use (except for Platinum® Taq, which was only quick spun). The LightCycler™ PCR mix was prepared as soon as the reagents were thawed.

LightCycler ™ PCR Master Mix - B. pertussis IS481  
Number of reactions => 50  
Target volume => 5

| Ingredient | Stock | Stock Conc. | Mix | Mix Conc. | (µl) |
|---|---|---|---|---|---|
| Water | | | | | 456.5 |
| MgCl2 | 50 | mM | 4 | mM | 80 |
| 10X Platinum ® buffer | 10 | x | 1 | X | 100 |
| Primers | 25 | µM | 0.75 | µM | 30 |
| Platinum ® Taq | 5 | U/µl | 0.025 | U/µl | 5 |
| dNTP plus | 10 | mM | 0.2 | mM | 20 |
| BSA | 2 | % | 0.025 | % | 12.5 |
| HK-UNG | 10 | % | 0.2 | % | 20 |
| BP IS F probe | 20 | µM | 0.2 | µM | 10.0 |
| BP IS R probe | 20 | µM | 0.3 | µM | 15.0 | dNTP plus = 1X each of dATP, dCTP, and dGTP, 3X of dUTP

LightCycler ™ Hybridization Master Mix - B. parapertussis IS1001  
Number of reactions => 50  
Target volume => 5

| Ingredient | Stock | Stock Conc. | Mix | Mix Conc. | (µl) |
|---|---|---|---|---|---|
| Water | | | | | 447.5 |
| MgCl2 | 50 | mM | 4 | mM | 80 |
| 10X Platinum ® buffer | 10 | x | 1 | X | 100 |
| Primers | 25 | µM | 0.75 | µM | 30 |
| DMSO | 100 | % | 1 | % | 10 |
| Platinum ® Taq | 5 | U/µl | 0.025 | U/µl | 5 |
| dNTP plus | 10 | mM | 0.2 | mM | 20 |
| BSA | 2 | % | 0.025 | % | 12.5 |
| HK-UNG | 10 | % | 0.2 | % | 20 |
| BPP F probe | 20 | µM | 0.2 | µM | 10.0 |
| BPP R probe | 20 | µM | 0.3 | µM | 15.0 | dNTP plus = 1X each of dATP, dCTP, and dGTP, 3X of dUTP

Alternatively, a single master mix can be generated to detect either or both *B. pertussis* or *B. parapertussis* in a biological sample.

LightCycler ™ Hybridization Master Mix  
B. pertussis IS481 and B. parapertussis IS1001  
Number of reactions => 50  
Target volume => 5

| Ingredient | Stock | Stock Conc. | Mix | Mix Conc. | (µl) |
|---|---|---|---|---|---|
| Water | | | | | 421.5 |
| MgCl$_2$ | 50 | mM | 4 | mM | 80 |
| 10X Platinum ® buffer | 10 | x | 1 | X | 100 |
| Primers (*B. pertussis*) | 25 | µM | 0.5 | µM | 20 |
| Primers (*B. parapertussis*) | 25 | µM | 0.5 | µM | 20 |
| Platinum ® Taq | 5 | U/µl | 0.03 | U/µl | 6 |
| dNTP plus | 10 | mM | 0.2 | mM | 20 |
| BSA | 2 | % | 0.025 | % | 12.5 |
| HK-UNG | 10 | % | 0.2 | % | 20 |
| BP F probe | 20 | µM | 0.2 | µM | 10 |
| BP R probe | 20 | µM | 0.3 | µM | 15 |
| BPP F probe | 20 | µM | 0.2 | µM | 10 |
| BPP R probe | 20 | µM | 0.3 | µM | 15 |

Example 4

Quality Control

A positive control of both *B. pertussis* (ATCC #9797) and *B. parapertussis* (ATCC#15311) were extracted and processed through the LightCycler™ detection in each clinical run. A melting curve analysis was used to differentiate the two organisms. If amplification of the positive control was not detected within 4 cycles of the expected number of cycles for detection of positive controls, or does not amplify, the run was repeated.

A fresh culture of the ATCC strains of *B. pertussis* and *B. parapertussis* were grown on charcoal agar at 37° C. in a $CO_2$ incubator. Several colonies were resuspended in sterile saline and adjusted to a MacFarland standard of 0.5 (ca.1.5×10$^8$ organisms/ml) using the Vitek Colorimeter (85% T±2). A 10-fold dilution series was prepared using molecular grade water (50 µl dilution into 450 µl water). Recovery studies were performed by adding 20 µl of each dilution of the series to Sample Buffer and extracting the DNA. The optimal concentration of *B. pertussis* and *B. parapertussis* was determined and a stock solution of the appropriately diluted culture was made in molecular grade water and stored at 4° C.

A positive control was generated by cloning IS481 or IS1001 nucleic acid molecules into a vector using the Invitrogen TOPO TA Cloning kit (Cat. #K4500-01). The 234 by PCR amplicon of *B. pertussis* and the 200 by PCR amplicon of *B. parapertussis* were each inserted into a plasmid vector (pCR 2.1-TOPO). The recombinant vector was transformed into chemically competent *E. coli* and grown overnight on a LB agar plate containing 50 µg/ml of kanamycin. The white colonies containing the confirmed recombinant plasmid were grown overnight in LB broth containing kanamycin and purified with the Promega Wizard Plus MiniPrep DNA purification system (Cat. #A7500). The stock concentration of the positive plasmid control was determined in molecules/µl. A ten-fold serial dilution was prepared using 20 µl of the suspension and 180 µl of sterile RNAse-free water. This dilution series was carried through until no amplification product was detected. Each dilution was tested with the *Bordetella* LightCycler™ assay and the optimal positive control dilution was determined. A working solution of 1.0 ml of this dilution was prepared and stored at 4° C.

Alternatively, the positive control was extracted from a culture (20 µl control plus 180 µl Isoquick Sample Buffer) and processed in parallel with the clinical specimens to provide a consistent means of monitoring assay performance. Negative controls were included in each clinical run. Negative controls consisted of 5-10% of the batch and were interspersed in the LightCycler™ apparatus with patient samples. These controls tested for hybridization mix contamination and specimen-to-specimen carryover contamination. If a negative control(s) yielded a positive reaction, extraction reagents were replaced and the samples and controls from the run in question were re-extracted.

Isoquick solution Sample Buffer A was extracted and used as a negative control. This was to confirm that extraction reagents were not contaminated with previously amplified product. Alternatively, 5 µl of water was added directly to the Master Mix and amplified as a negative control. All specimens (patient's and controls) were handled using Universal Precautions. Sterile gloves were worn when handling samples and performing all procedures. Gloves were changed frequently.

dUTP incorporation and uracil N-glycosylase treatment with a thermolabile UNG (Epicentre Technologies; Madison, Wis.; Catalog #HU5910K) were used to prevent amplicon carryover in the LightCycler™ assays described herein. Although not required, the routine implementation of these precautions diminishes the risk of false-positive results. False-positive results have been a significant and often cited problem in many laboratories using PCR techniques and can seriously compromise the reliability of testing performed in a clinical environment.

Example 5

Interpreting and Reporting Results

A clinical specimen that displayed a melting temperature of 75°±2° C. was interpreted as positive for *B. pertussis* and/or a melting temperature of 64°±2° C. was interpreted as positive for *B. parapertussis* DNA.

The *B. pertussis* IS481 assay is specific for *B. pertussis* and a positive signal is reported as *B. pertussis*. Although the primers and probes are specific for the insertion sequence of *B. pertussis* IS481, cross-reactivity with *B. holmesii* can occur with *B. pertussis* IS481 PCR assays. Cephalexin, the antibiotic widely used in culture media, has an inhibitory effect on *B. holmesiii*. In one evaluation, *B. holmesii* positivity rate in nasopharyngeal specimens was 0.29%. The clinical significance of *B. holmesii* has yet to be determined although it has been associated with septicemia, respiratory failure and symptoms similar to *B. pertussis* infection (i.e., cough).

The *B. parapertussis* IS1001 assay is specific for *B. parapertussis* species and a positive signal is reported as *B. parapertussis*. Because the primers and probes are specific for *B. parapertussis*, and no cross-reactions have been observed with these reagents, a positive test will provide results of the specific nucleic acid. Therefore, positive results can be reported as *B. parapertussis*.

A clinical specimen or control with no melting curve above baseline should be interpreted as negative for the presence of *B. pertussis* or *B. parapertussis* DNA. Results are strictly qualitative. A negative result does not negate the presence of the organism or active disease. Test results should be used as an aid in diagnosis and not be considered a stand-alone diagnostic test. A single assay should not be used as the only criteria to form a clinical conclusion, but results should be correlated with serologic tests, patient symptoms, and clinical presentation.

Example 6

Method Validation

The LightCycler™ PCR assay for detection of *B. pertussis* and/or *B. parapertussis* was compared to culture/DFA, to conventional PCR of the IS481 gene of *B. pertussis*, and to a LightCycler™ PCR assay for detection of the pertussis toxin gene (PTG). A combined gold standard was used to compare the LightCycler™ PCR assay to the other detection methods. This gold standard is defined as ≧1 positive result in any combination of results from culture/DFA, PTG, and conventional PCR.

Compared to culture/DFA and a LightCycler™ PCR assay for detection of PTG, the LightCycler™ PCR assay for detection of *B. pertussis* and *B. parapertussis* using IS481 and IS1001, respectively, was 100% sensitive and 72% specific (p<0.0001 using a kappa statistic). The positive predictive value (ppv) and the negative predictive value (npv) were 30% and 100%, respectively. Compared to the LightCycler™ PCR assay, conventional PCR of the IS481 gene had a sensitivity of 96%, specificity of 82%, ppv of 83%, and an npv of 95% (p=0.0654). Compared to LightCycler™ PCR and PTG LightCycler™ PCR, culture/DFA had a sensitivity of 25%, specificity of 100%, ppv of 100%, and an npv of 70% (p<0.0001). Compared to LightCycler™ PCR and culture/DFA, the PTG LightCycler™ assay had a sensitivity of 28%, specificity of 100%, ppv of 100%, and an npv of 71% (p<0.0001). Using dilutions of well-characterized American Type Culture Collection (ATCC) and CDC positive controls, the sensitivity of the IS481/IS1001 assay was 1 organism/µl for both the detection of *B. pertussis* and *B. parapertussis*.

A low level positive control of *B. pertussis* and *B. parapertussis* was run multiple times within a run, two times within a day and on three consecutive days. The variability was determined to be in the acceptable range of ±4 cycles. The analytical detection limit of the LightCycler™ PCR assay, using dilutions of a McFarland 0.5 standard of fresh cultures, was 1 organism per reaction. The average number of templates per organism was 80 in *B. pertussis* and 20 in *B. parapertussis*.

Ninety-two Isoquick extracted nasopharyngeal samples were spiked with *B. pertussis* and *B. parapertussis* and tested for the presence of inhibitors. 13 samples did not amplify under such conditions, giving an inhibition rate of 14%. The choice of transport swab and medium may affect inhibition (e.g., calcium alginate swabs, cotton swabs, and aluminum shaft swabs may be inhibitory to PCR).

Example 7

*Bordetella* LightCycler Assay #2 with Recovery Template

200 µl sterile water was added to an original tube containing a nasopharyngeal swab, and the tube was vortexed well. 200 µl of the swab material was transferred to a screw-capped tube containing 4 µl of recovery template ($5 \times 10^3$ targets/µl), and the tube was capped and mixed briefly. Recovery template is modified template nucleic acid that is co-amplified in the same tube by the same set of primers used to amplify template nucleic acid. Recovery template, however, uses different probes for detection. The probes that hybridize to the recovery template (apoE-F and apoE 705) are labeled with fluorescein and LC-Red 705 so that amplification of the recovery template is measured on a different channel than the channel used to measure amplification of the template. Recovery template can be used to identify samples containing an inhibitory component.

100 µl of STAR Buffer (Roche Molecular Diagnostics, Indianapolis, Ind.) was placed into a MagNA Pure sample cartridge. 100 µl of the swab sample (containing recovery template at a final concentration of $1 \times 10^2$ targets/µl) was transferred into extraction wells, and the DNA extracted using MagNA Pure and the LightCycler Total Nucleic Acid Isolation kit.

The remaining 100 µl of the swab sample was placed in a 95° C. (±5° C.) heat block for 10 min. The tube was centrifuged for 3 min at 20,000×g to pellet any particulate material.

Example 8

Control Samples

Several types of positive controls were used. For a positive control of each organism, *B. pertussis* (ATCC Accession No. 9797) or *B. parapertussis* (ATCC Accession No. 15311) were grown on charcoal agar and diluted to a McFarland 0.5 (1.5×

$10^8$ cells/ml). The cultures were further diluted to a working concentration of $1.5\times10^6$ cells/ml and used as controls for extraction and amplification reactions of template from the boiled lysate procedure and from the MagNA Pure extraction. A positive control corresponding to each *Bordetella* organism included 198 µl sterile water+2 µl organism control ($1.5\times10^6$ cells/µl)+4 µl recovery template ($5\times10^3$ targets/µl).

In addition to the organism controls, a plasmid containing *Bordetella* sequences was used as a positive control. The plasmid contains sequences from both IS481 (*B. pertussis*) and IS1001 (*B. parapertussis*) (Roche Molecular Diagnostics). A positive extraction control corresponding to the plasmid included 198 µl sterile water+2 µl plasmid ($2\times10^3$ targets/µl)+4 µl recovery template ($5\times10^3$ targets/µl).

A negative control included 200 µl sterile water+4 µl recovery template ($5\times10^3$ targets/µl).

Example 9

*Bordetella* LightCycler Assay #2

Tables 3 and 4 describe the sequences of the primers and probes used for detection of *B. pertussis* and *B. parapertussis*, respectively.

TABLE 3

| Type   | Name      | Sequences (5'→3')              | SEQ ID NO: |
|--------|-----------|--------------------------------|------------|
| Primer | BP IS1    | ccagttcctcaaggacgc             | 1          |
| Primer | BP IS2    | gagttctggtaggtgtgagcgta        | 2          |
| Probe  | BP-F(WT)  | caccgctttacccgaccttaccgcccac   | 3          |
| Probe  | BP853mm29 | gaccaatggcaaggctcgaacgcttcatc  | 11         |

TABLE 4

| Type   | Name    | Sequences (5'→3')   | SEQ ID NO: |
|--------|---------|---------------------|------------|
| Primer | BPP IS1 | ggcgatatcaacgggtga  | 5          |
| Primer | BPP IS2 | cagggcaaactcgtccatc | 6          |
| Probe  | VPP03   | ggttggcataccgtcaaga | 12         |
| Probe  | VPP04   | gctggacaaggctcg     | 13         |

The components of the *Bordetella* LightCycler Assay #2 reaction mix are as follows.

| Reagent                                           | Volume |
|---------------------------------------------------|--------|
| Water                                             | 11 µl  |
| Primer/Probe Mix[a]                               | 2 µl   |
| FastStart DNA Master Hybridization Probes[b]      | 2 µl   |
| Total                                             | 15 µl  |

[a]primer/probe mix includes: 2.5 mM $MgCl_2$; 0.3 µM each BP IS1 and BPP IS1; 0.5 µM each BP IS2 and BPP IS2; 0.2 µM each BP-F, VPP03, apoE-F, and apoE 705; and 0.4 µM each BP853mm29 and VPP04.
[b]magnesium is present in the FastStart DNA Master Hybridization Probe solution at a concentration of 1 mM.

As an alternative to adding the recovery template to the sample prior to extraction, recovery template can be added to the PCR reaction mix at a final concentration of $5\times10^3$ targets/µl.

5 µl from the boiled lysate, the MagNA Pure extraction, or the positive or negative control samples, was mixed with 15 µl of the *Bordetella* LightCycler PCR reaction mix described above, placed in a LightCycler carousel, and amplified as follows.

| A. Initial | 95° C. | 10 min |          |                   |
|------------|--------|--------|----------|-------------------|
| B. PCR     |        |        |          | 45 cycles         |
|            | 95° C. | 10 sec |          |                   |
|            | 55° C. | 15 sec |          | Single signal     |
|            | 72° C. | 15 sec |          |                   |
| C. Melt    | 95° C. | 0 sec  | 20°/sec  |                   |
|            | 59° C. | 20 sec | 20°/sec  |                   |
|            | 45° C. | 20 sec | 0.2°/sec |                   |
|            | 85° C. | 0 sec  | 0.1°/sec | Continuous Signal |
| D. Melt 2  | 95° C. | 0 sec  | 20°/sec  |                   |
|            | 59° C. | 20 sec | 20°/sec  |                   |
|            | 45° C. | 20 sec | 0.2°/sec |                   |
|            | 85° C. | 0 sec  | 0.2°/sec | Continuous Signal |
| E. Cool    | 40° C. | 10 sec |          |                   |

Results of the experiments are shown in Table 5. The addition of the recovery template to the specimens prior to nucleic acid extraction did not inhibit the extraction or the amplification of a product. A sample was considered to contain an inhibitory component if the recovery template amplification product was not generated in the absence of target template.

TABLE 5

| | | *Bordetella* LightCycler Assay #2 | | |
|---|---|---|---|---|
| Sample | *Bordetella* LightCycler Assay #1 | MagNA Pure | MagNA Pure (w/recovery template) | Boil | Boil (w/ recovery template) |
|---|---|---|---|---|---|
| 1  | − |          | + | −         | + |
| 2  | + | *B. pert* | − | *B. pert* | − |
| 3  | + | *B. pert* | + | *B. pert* | + |
| 4  | − |          | + | −         | + |
| 5  | − |          | + | −         | + |
| 6  | − |          | + | −         | + |
| 7  | + | *B. para* | + | *B. para* | + |
| 8  | + | *B. pert* | + | *B. pert* | − |
| 9  | + | *B. pert* | + | *B. pert* | − |
| 10 | − |          | + | −         | + |
| 11 | − |          | + | −         | + |
| 12 | + | *B. pert* | + | *B. pert* | + |
| 13 | − |          | + | −         | + |
| 14 | + | *B. pert* | + | *B. pert* | + |
| 15 | − |          | + | −         | + |
| 16 | − |          | + | −         | + |
| 17 | − |          | + | −         | + |
| 18 | + | *B. pert* | + | *B. pert* | + |
| 19 | − |          | + | −         | + |
| 20 | + | *B. pert* | + | *B. pert* | + |
| 21 | − |          | + | −         | + |
| 22 | + | *B. pert* | − | *B. pert* | − |
| 23 | + | *B. pert* | + | *B. pert* | + |
| 24 | + | *B. pert* | + | *B. pert* | + |
| 25 | − |          | + | −         | + |
| 26 | − |          | + | −         | + |
| 27 | − |          | + | −         | + |
| 28 | − |          | + | −         | + |
| 29 | + | *B. para* | + | *B. para* | + |
| 30 | + | *B. pert* | + | *B. pert* | + |

Example 10

Specificity of *Bordetella* LightCycler Assay #2

Experiments were performed to determine if the *Bordetella* primers and probes cross-reacted with nucleic from similar organisms or from organisms commonly found in the specimens tested.

5 µl from the boiled lysate or from the MagNA Pure extraction was added to 15 µl of the PCR reaction mix described above in Example 9. Samples were placed into a LightCycler carousel and cycled as described above in Example 9. Nucleic acid had previously been shown to be amplifiable in the bacterial organisms listed in Table 6 using 16S rRNA amplification by conventional or LightCycler PCR assays. $2 \times 10^3$ targets/µl of the positive control plasmid described above in Example 8 was used.

TABLE 6

| Organism | Result |
|---|---|
| Pseudomonas aeruginosa | − |
| Chlamydia pneumoniae | − |
| Klebsiella pneumoniae | − |
| Escherichia coli | − |
| Haemophilus influenza | − |
| Aeromonas species | − |
| Staphylococcus aureus | − |
| Legionella jordanis | − |
| S. maltophilia | − |
| Klebsiella oxytoca | − |
| Pseudomonas cepacia | − |
| Staphylococcus epidermidis | − |
| Neisseria gonorrhoeae | − |
| Pseudomonas fluorescens | − |
| C. pseudodiptheriae | − |
| Morganella species | − |
| Proteus vulgaris | − |
| Mycoplasma pneumonia | − |
| Campylobacter jejuni | − |
| M. catarrhalis | − |
| Human DNA | − |
| Bordetella pertussis | + |
| Legionella pneumophila | − |
| Bordetella bronchioseptica | − |
| Neisseria meningitidis | − |
| Bordetella holmesii | + |
| Acinetobacter species | − |
| Proteus mirabilis | − |
| Corynebacterium diphtheriae | − |
| Bordetella parapertussis | + |

Other than the *B. pertussis* and *B. parapertussis* positive controls and the closely related *B. holmesii*, which was previously detected with the *Bordetella* Lightcycler Assay #1, none of the organisms shown in Table 6 cross-reacted with the *Bordetella* primers and probes used in the *Bordetella* Light-Cycler Assay #2.

Example 11

Diagnositic Sensitivity of the *Bordetella* LightCycler Assay #2

Experiments were performed to determine the sensitivity and specificity of the *Bordetella* LightCycler Assay #2 compared to culture and other amplification methods. 110 nasopharyngeal swabs from patient samples sent in for *Bordetella* testing were examined using a culture method, and a portion of those samples were analyzed by a conventional PCR method and the *Bordetella* LightCycler Assays #1 and #2 disclosed herein. The nasopharyngeal swabs were initially cultured on charcoal agar plates containing cephalexin and blood agar, incubated at 37° C. and examined daily for 5 days for the presence of *B. pertussis* and/or *B. parapertussis*.

After swiping on agar plates, the nasopharyngeal swabs were swished in a tube containing 500 µl sterile water. 200 µl was removed from the tube (n=35) and processed by boiling at 100° C. for 10 min. After boiling, the sample was centrifuged for 1 minute at 20,800×g. The DNA present in 200 µl of the remaining nasopharyngeal swab sample was extracted using the Isoquick Nucleic Acid Extraction Kit (ORCA Research, Inc., Bothell, Wash.). These samples were stored at −20° C. for up to 48 months.

Using 99 of the 110 samples described above, 5 µl of the boiled lysate or the Isoquick extraction eluate was added to 15 µl of the PCR Reaction Mix described above in Example 3. The samples were analyzed by the *Bordetella* LightCycler Assay described above in Example 1 (*Bordetella* LightCycler Assay #1).

Another 5 µl of the boiled lysate or the IsoQick extraction eluate was added to 15 µl of the PCR Reaction Mix described above in Example 8. The samples were analyzed by the *Bordetella* LightCycler Assay described above in Example 8 (*Bordetella* LightCycler Assay #2).

A conventional PCR assay was used and amplified IS481 nucleic acid sequences. Following amplification by PCR, the sample was electrophoresed on an agarose gel, Southern blotted, and detected by enzyme chemiluminescence (Amersham Corporation, Arlington Heights, Ill.). The conventional PCR protocol for detecting *B. pertussis* had approximately a 2-5 day turnaround time.

Results of culture methods versus the *Bordetella* LightCycler Assay #2 are shown in Table 7. Results of experiments comparing *Bordetella* LightCycler Assay #1, *Bordetella* LightCycler Assay #2, and the conventional PCR assay are shown in Table 8.

TABLE 7

| | | Culture | | | |
|---|---|---|---|---|---|
| | | B. pertussis | B. parapertussis | Negative | Total |
| Bordetella LightCycler Assay #2 | B. pertussis | 18 | 0 | 23 | 41 |
| | B. parapertussis | 0 | 4 | 1 | 5 |
| | Negative | 0 | 0 | 59 | 59 |
| | Total | 18 | 4 | 83 | 105* |

*The 5 samples unaccounted for were considered indeterminate since recovery template was not detected.

TABLE 8

| | | Bordetella LightCycler Assay #1 | | | |
|---|---|---|---|---|---|
| | | B. pertussis | B. parapertussis | Negative | Total |
| Bordetella LightCycler Assay #2 | B. pertussis | 38 | 0 | 3 | 41 |
| | B. parapertussis | 0 | 2 | 1 | 3 |
| | Negative | 9 | 2 | 44 | 55 |
| | TOTAL | 47 | 4 | 48 | 99 |

Five samples were found to inhibit PCR amplification using the *Bordetella* Lightcycler Assay #2 based upon a lack of detection of the recovery template. The correlation between the *Bordetella* LightCycler Assay #1 and the *Bordetella* LightCycler Assay #2 was good. The integrity of some of the samples was questionable, with nucleic acid samples archived for a longer period of time sometimes resulting in a negative result.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An article of manufacture, comprising:
a pair of IS481 primers, wherein said pair of IS481 primers comprise a first IS481 primer and a second IS481 primer, wherein said first IS481 primer comprises the sequence 5'-CCA GTT CCT CAA GGA CGC-3' (SEQ ID NO:1), and wherein said second IS481 primer comprises the sequence 5'-GAG TTC TGG TAG GTG TGA GCG TA-3' (SEQ ID NO:2);
a pair of IS481 probes, wherein said pair of IS481 probes comprises a first IS481 probe and a second IS481 probe, wherein said first IS481 probe comprises the sequence 5'-CAC CGC TTT ACC CGA CCT TAC CGC CCA C-3' (SEQ ID NO:3), and wherein said second IS481 probe comprises the sequence 5'-GAC CAA TGG CAA GGC TCG AAC GCT TCA TC-3' (SEQ ID NO:11); and
a donor fluorescent moiety and a corresponding acceptor fluorescent moiety.

2. The article of manufacture of claim 1, wherein said first IS481 probe is labeled with said donor fluorescent moiety and wherein said second IS481 probe is labeled with said corresponding acceptor fluorescent moiety.

3. The article of manufacture of claim 1, further comprising a package insert having instructions thereon for using said pair of IS481 primers and said pair of IS481 probes to detect the presence or absence of *B. pertussis* in a biological sample.

4. An article of manufacture, comprising:
a pair of IS481 primers and a pair of IS481 probes,
wherein said pair of IS481 primers comprise a first IS481 primer and a second IS481 primer, wherein said first IS481 primer comprises the sequence 5'-CCA GTT CCT CAA GGA CGC-3' (SEQ ID NO:1), and wherein said second IS481 primer comprises the sequence 5'-GAG TTC TGG TAG GTG TGA GCG TA-3' (SEQ ID NO:2);
wherein said pair of IS481 probes comprises a first IS481 probe and a second IS481 probe, wherein said first IS481 probe comprises the sequence 5'-CAC CGC TTT ACC CGA CCT TAC CGC CCA C-3' (SEQ ID NO:3), and wherein said second IS481 probe comprises the sequence 5'-GAC CAA TGG CAA GGC TCG AAC GCT TCA TC-3' (SEQ ID NO:11); and
a donor fluorescent moiety and a corresponding acceptor fluorescent moiety; and
a pair of IS1001 primers and a pair of IS1001 probes,
wherein said pair of IS1001 primers comprise a first IS1001 primer and a second IS1001 primer, wherein said first IS1001 primer comprises the sequence 5'-GGC GAT ATC AAC GGG TGA-3' (SEQ ID NO:5), and wherein said second IS1001 primer comprises the sequence 5'-CAG GGC AAA CTC GTC CAT C-3' (SEQ ID NO:6);
wherein said pair of IS1001 probes comprise a first IS1001 probe and a second IS1001 probe, wherein said first IS1001 probe comprises the sequence 5'-GGT TGG CAT ACC GTC AAG A-3' (SEQ ID NO:12), and wherein said second IS1001 probe comprises the sequence 5'-GCT GGA CAA GGC TCG-3' (SEQ ID NO:13); and
a donor fluorescent moiety and a corresponding acceptor fluorescent moiety.

5. The article of manufacture of claim 4, further comprising a package insert having instructions thereon for using said pair of IS 481 primers, said pair of IS481 probes, said pair of IS1001 primers and said pair of IS1001 probes to distinguish between *B. pertussis* and *B. parapertussis* in a biological sample.

6. The article of manufacture of claim 4, further comprising a package insert having instructions thereon for using said pair of IS481 probes and said pair of IS1001 probes to distinguish between *B. pertussis* and *B. parapertussis* in a biological sample.

* * * * *

```
                        SEQUENCE LISTING

<160> NUMBER OF SEQ ID NOS: 13

<210> SEQ ID NO 1
<211> LENGTH: 18
<212> TYPE: DNA
<213> ORGANISM: Artificial Sequence
<220> FEATURE:
<223> OTHER INFORMATION: Oligonucleotide

<400> SEQUENCE: 1
ccagttcctc aaggacgc                                                  18

<210> SEQ ID NO 2
<211> LENGTH: 23
<212> TYPE: DNA
<213> ORGANISM: Artificial Sequence
<220> FEATURE:
<223> OTHER INFORMATION: Oligonucleotide

<400> SEQUENCE: 2
gagttctggt aggtgtgagc gta                                            23

<210> SEQ ID NO 3
<211> LENGTH: 28
<212> TYPE: DNA
<213> ORGANISM: Artificial Sequence
<220> FEATURE:
<223> OTHER INFORMATION: Oligonucleotide

<400> SEQUENCE: 3
caccgcttta cccgaccttaa ccgcccac                                      28

<210> SEQ ID NO 4
<211> LENGTH: 28
<212> TYPE: DNA
<213> ORGANISM: Artificial Sequence
<220> FEATURE:
<223> OTHER INFORMATION: Oligonucleotide

<400> SEQUENCE: 4
gaccaatggc aaggccgaac gcttcatc                                       28

<210> SEQ ID NO 5
<211> LENGTH: 18
<212> TYPE: DNA
<213> ORGANISM: Artificial Sequence
<220> FEATURE:
<223> OTHER INFORMATION: Oligonucleotide

<400> SEQUENCE: 5
ggcgatatca acgggtga                                                  18

<210> SEQ ID NO 6
<211> LENGTH: 19
<212> TYPE: DNA
<213> ORGANISM: Artificial Sequence
<220> FEATURE:
<223> OTHER INFORMATION: Oligonucleotide

<400> SEQUENCE: 6
cagggcaaac tcgtccatc                                                 19
```

<210> SEQ ID NO 7
<211> LENGTH: 24
<212> TYPE: DNA
<213> ORGANISM: Artificial Sequence
<220> FEATURE:
<223> OTHER INFORMATION: Oligonucleotide

<400> SEQUENCE: 7
gttcttcgaa ctgggttggc atac 24

<210> SEQ ID NO 8
<211> LENGTH: 22
<212> TYPE: DNA
<213> ORGANISM: Artificial Sequence
<220> FEATURE:
<223> OTHER INFORMATION: Oligonucleotide

<400> SEQUENCE: 8
gtcaagacgc tggacaaggc tc 22

<210> SEQ ID NO 9
<211> LENGTH: 1073
<212> TYPE: DNA
<213> ORGANISM: B. pertussis

<400> SEQUENCE: 9
gcgaggccgg ctatctgtga agattcaata ggttgtatgc atggttcatc cgaaccggat 60
ttgagaaact ggaaatcgcc gaccccccag ttcactcaag gagcccggcc ggatgaacac 120
ccataagcat gcccgattga ccttcctacg tcgactcgaa atggtccagc aattgatcgc 180
ccatcaagtt tgtgtgcctg aagcggcccg cgcctatggg gtcaccgcgc cgactgtgcg 240
caaatggctg ggccgcttcc tggctcaggg ccaggcgggc ttggccgatg cgtcctcgcg 300
cccgacggtc tcgccccgag cgattgcgcc ggccaaggcg ctggctatcg tggagctgcg 360
ccgcaagcgg ctgacccaag cgcgcatcgc ccaggcgctg ggcgtgtcag ccagcaccgt 420
cagccgcgtc ctggcccgcg ccggtctgtc gcacctggcc gacctggagc cggccgagcc 480
ggtggtgcgc tacgagcatc aggcccccgg cgatctgctg cacatcgaca tcaagaagct 540
gggacgtatc cagcgccctg gccaccgggt cacgggcaac cgacgcgata ccgttgaggg 600
ggccggctgg gacttcgtct tcgtggccat cgatgaccac gcccgcgtgg ccttcaccga 660
catccccccc gacgagcgct tccccagcgc cgtccagttc ctcaaggacg cagtggccta 720
ctaccagcgc ctgggcgtga ccatccagcg cttgctcacc gacaatggct cggcctttcg 780
cagccgcgcc ttcgccgcgc tgtgccatga gctgggcatc aagcaccgct ttacccgacc 840
ttaccgccca cagaccaatg gcaaggccga acgcttcatc cagtcggcct tgcgtgagtg 900
ggcttacgct cacacctacc agaactccca acaccgagcc gatgccatga aatcctggct 960
acaccactac aactggcatc gaccccacca aggcatcggg cgcgctgtac ccatctccag 1020
actcaacctg gacgaataca acctattgac agttcacagc tatccggacc ggc 1073

<210> SEQ ID NO 10
<211> LENGTH: 1306
<212> TYPE: DNA
<213> ORGANISM: B. parapertussis

<400> SEQUENCE: 10
ggttcatcgc gcaataacgt ggaggggttt ggcaattttc gtattcttga cggcaggtat 60
ttgacatcag gagtgcaggg agatgctgga tcgcaagttg atggagtcgc tgggaggctg 120
gcagggctat ggcgtcgaac gcgtggaatg gcccgaagac ccagggcgca cgctgtcgat 180

-continued

```
ctatttgaag ccaacggcca aggtgatgct gtgcgagcag tgcggcgcgc ggtgtcgcca      240
ggtgcatgag accacggttc gacgggtgcg agatctgccg atattcgagt atcgggtcgt      300
tctgcacgtg ccgcgccgac gcttgtggtg tgagcaatgc ggcggcccgc gcctggagcg      360
gcttgcctgg ctggggcgat atcaacgggt gacggatcgg ctggcgcagg cctgcagcca      420
attgctgcaa tcgagcaacg tgcaggcggt ggcgaggttc ttcgaactgg gttggcatac      480
cgtcaagacg ctggacaagg ctcggctgcg tgcgtcggtg cgcgaaccgg attggtccaa      540
gatcgagtat ttggcgatgg acgagtttgc cctgcacaaa gggcatcgct acgcgacagt      600
ggtggtcgat ccgatcggca ggcaggtgct gtggattggc ccaggacgct cacgcgagac      660
ggcccgggcg ttcttcgaac aattgccgcc tgggccgcc caacgcatca aggccgttgc       720
catcgacatg accaccgcct acgagttgga gatccaggcc cacagcccac aggcggagat      780
cgtctatgac ttgttccatg tcgtggccaa gtatggacga gaggtcattg atcgggtgcg      840
cgtggatcag gccaatcaac tacgccagga tcgtcccgca cgcaggatca tcaaatcgag      900
tcgctggctg ctgctgcgca accgtgacaa cctggatcgg cagcaggccg tccggctcga      960
cgaattgctg caagccaacc agccgctgct gacggtctat gtcctgcgtg acgaactcaa     1020
acggctctgg ttctaccaaa gacctgcctg gcaagacaa gcctggaacc actggtacga     1080
gcaggccgag caaagcggaa tagccgcctt gaacaccttc gctcagcgct tgaaaggcta    1140
tctgcacggc atcctggcca gatgccgaca tcccctgaac accagcattg tcgagggcat    1200
caacaacact atcaaggtca tcaagcggcg cgcttacggc taccgcgacc aggaatactt    1260
cttcctcaaa atccgtgccg ccttcccccgg caatgcgcga tgaacc                   1306
```

```
<210> SEQ ID NO 11
<211> LENGTH: 29
<212> TYPE: DNA
<213> ORGANISM: Artificial Sequence
<220> FEATURE:
<223> OTHER INFORMATION: Oligonucleotide

<400> SEQUENCE: 11
gaccaatggc aaggctcgaa cgcttcatc                                         29

<210> SEQ ID NO 12
<211> LENGTH: 19
<212> TYPE: DNA
<213> ORGANISM: Artificial Sequence
<220> FEATURE:
<223> OTHER INFORMATION: Oligonucleotide

<400> SEQUENCE: 12
ggttggcata ccgtcaaga                                                    19

<210> SEQ ID NO 13
<211> LENGTH: 15
<212> TYPE: DNA
<213> ORGANISM: Artificial Sequence
<220> FEATURE:
<223> OTHER INFORMATION: Oligonucleotide

<400> SEQUENCE: 13
gctggacaag gctcg                                                        15
```